(12) United States Patent
Kuhara et al.

(10) Patent No.: US 10,203,385 B2
(45) Date of Patent: Feb. 12, 2019

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara-Shi, Tochigi-Ken (JP)

(72) Inventors: Shigehide Kuhara, Tochigi (JP); Shuhei Nitta, Tokyo (JP); Taichiro Shiodera, Tokyo (JP); Yukinobu Sakata, Kanagawa (JP); Tomoyuki Takeguchi, Kanagawa (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 412 days.

(21) Appl. No.: 14/978,222

(22) Filed: Dec. 22, 2015

(65) Prior Publication Data
US 2016/0109544 A1 Apr. 21, 2016

Related U.S. Application Data

(63) Continuation of application No. PCT/JP2015/050819, filed on Jan. 14, 2015.

(30) Foreign Application Priority Data

Jan. 14, 2014 (JP) ................ 2014-004526

(51) Int. Cl.
*A61B 5/055* (2006.01)
*G01R 33/483* (2006.01)
*A61B 5/00* (2006.01)

(52) U.S. Cl.
CPC ........ *G01R 33/4835* (2013.01); *A61B 5/0037* (2013.01); *A61B 5/0044* (2013.01);
(Continued)

(58) Field of Classification Search
CPC ............. G01R 33/4835; G01R 33/4833; A61B 5/489; A61B 5/0037; A61B 5/7271; A61B 5/0044; A61B 5/055
(Continued)

(56) References Cited

U.S. PATENT DOCUMENTS

| 5,107,838 | A | 4/1992 | Yamaguchi |
| 7,280,862 | B2 | 10/2007 | Gupta et al. |

(Continued)

FOREIGN PATENT DOCUMENTS

| JP | 2011-120825 | 6/2011 |
| JP | 2012-110688 | 6/2012 |

(Continued)

OTHER PUBLICATIONS

International Search Report for PCT/JP2015/050819 dated Apr. 7, 2015, 4 pages.

(Continued)

*Primary Examiner* — Farhana Hoque
(74) *Attorney, Agent, or Firm* — Nixon & Vanderhye P.C.

(57) ABSTRACT

A magnetic resonance apparatus of the present embodiment includes: a gantry which includes a static field magnet, a gradient coil and an RF coil to image an object; processing circuitry; a memory that stores processor-executable instructions that, when executed by the processing circuitry, cause the processing circuitry to detect at least one position of an aortic valve and a pulmonary valve from three-dimensional image data including a heart of the object, as at least one characteristic region inside the heart, specify a position of an imaging cross-section substantially orthogonal to a blood-stream path inside the heart based on the position of the aortic valve or the pulmonary valve, and cause the gantry to image the imaging cross-section of the object at the specified position of the imaging cross-section.

19 Claims, 17 Drawing Sheets

(52) U.S. Cl.
CPC .............. *A61B 5/055* (2013.01); *A61B 5/489* (2013.01); *A61B 5/7271* (2013.01); *G01R 33/4833* (2013.01)

(58) Field of Classification Search
USPC .......................................... 324/309; 600/410
See application file for complete search history.

(56) References Cited

U.S. PATENT DOCUMENTS

| 8,928,318 | B2 | 1/2015 | Nitta et al. | |
|---|---|---|---|---|
| 2006/0100503 | A1 | 5/2006 | Takai et al. | |
| 2009/0262980 | A1* | 10/2009 | Markowitz | A61B 5/0422 382/103 |
| 2012/0108946 | A1* | 5/2012 | Kuhara | A61B 5/0037 600/410 |
| 2013/0303885 | A1 | 11/2013 | Hoshino et al. | |
| 2014/0051978 | A1 | 2/2014 | Takai et al. | |

FOREIGN PATENT DOCUMENTS

| JP | 2013-236932 | 11/2013 |
|---|---|---|
| JP | 2013-255853 | 12/2013 |

OTHER PUBLICATIONS

S. Nitta et al., "Automatic slice alignment method for cardiac magnetic resonance imaging", *Magn Reson Mater Phy* DOI: 10.1007/s10334-012-0361-4, Dec. 17, 2012, 13 pages.

S. Nitta et al., "Automatic 14-plane slice-alignment method for ventricular and valvular analysis in cardiac magnetic resonance imaging", *Journal of Cardiovascular Magnetic Resonance*, 2014, 16(Suppl): P1, published Jan. 16, 2014, 2 pages.

English Translation of International Preliminary Report on Patentability dated Jul. 28, 2016 for Application No. PCT/JP2015/050819.

* cited by examiner

IMAGE INDICATING PIXEL VALUES I(x, y)

IMAGE INDICATING GRADIENT DIRECTION Idir(x, y) OF PIXEL VALUES

IMAGE INDICATING MAGNITUDE Igrad(x, y) OF GRADIENT OF PIXEL VALUE I(x, y)

MAGNETIC RESONANCE IMAGING APPARATUS AND MAGNETIC RESONANCE IMAGING METHOD

CROSS-REFERENCE TO RELATED APPLICATIONS

This application is a Continuation Application of No. PCT/JP2015/50819, filed on Jan. 14, 2015, and the PCT application is based upon and claims the benefit of priority from Japanese Patent Application No. 2014-4526, filed on Jan. 14, 2014, the entire contents of which are incorporated herein by reference.

FIELD

Embodiments described herein relate generally to a magnetic resonance imaging apparatus and a magnetic resonance imaging method.

BACKGROUND

A magnetic resonance imaging apparatus is an imaging apparatus which excites nuclear spin of a patient placed in a static magnetic field with an RF (Radio Frequency) pulse having the Larmor frequency and generates a reconstructed image by using the magnetic resonance signals emitted from the patient due to the excitation.

In many cardiac examinations using a magnetic resonance apparatus, first, six reference planes useful for diagnosis are selected, and then imaging of various still images and moving images in accordance with diagnostic purposes is performed at the respective selected reference planes.

Here, the six reference planes means a vertical long axis plane, a horizontal long axis plane, a short axis plane, a two-chamber long axis plane, a three-chamber long axis plane and four-chamber long axis plane.

Conventionally, in order to set the six reference planes, the method of repeating processes of positioning and imaging in the following manner has been used. In this conventional method, the position of the vertical long axis plane is determined from an axial cross-sectional image, then the position of the horizontal long axis plane is determined from the vertical long axis view imaged at the determined position of the vertical long axis plane, then the position of the short axis plane is determined from the horizontal long axis view imaged at the determined position of the horizontal long axis plane, and positioning and imaging are repeated in this manner (this method is sometimes referred to as a chain oblique technique, because it is a method of repeating positioning and imaging of oblique cross-sections).

Conventional technology based on the chain oblique technique requires wide experience and highly advanced skills in order to secure accuracy of setting cross-sectional positions, in addition to its complicated procedure. This is because the positional error of the previously determined cross-section influences the position of the subsequently determined cross-section. In addition, because considerable time is required for setting the six reference planes, it imposes a significant burden on a patient.

Then, technology of detecting anatomical features of the heart and automating setting of the six reference planes has been developed.

However, the conventional technology merely relates to a technology for automatically setting the above six reference planes and does not relate to a technology for setting cross-sections useful for cardiac diagnosis other than the six reference planes. For example, although kinetic observation of valves such as an aortic valve and a pulmonary valve is required in examination of valvular disease, sufficient automation has not been achieved as to setting of cross-sections appropriate for the kinetic observation of these valves. In addition, although dynamic information on blood flow velocity and passage diameters adjacent to valves such as an aortic valve and a pulmonary valve is necessary for understanding cardiac hemodynamics, sufficient automation has not been achieved as to setting of imaging cross-sections appropriate for measuring blood flow velocity and passage diameters.

Then, a magnetic resonance apparatus, that can automatically set cross-sections useful for cardiac diagnosis such as a cross-section appropriate for the kinetic observation of valves and a cross-section appropriate for understanding cardiac hemodynamics other than the six reference planes, has been desired.

DETAILED DESCRIPTION

The magnetic resonance apparatus of the present embodiment includes: a gantry which includes a static field magnet, a gradient coil and an RF coil to image an object; processing circuitry; and a memory that stores processor-executable instructions that, when executed by the processing circuitry, cause the processing circuitry to detect at least one position of an aortic valve and a pulmonary valve from three-dimensional image data including a heart of the object, as at least one characteristic region inside the heart, specify a position of an imaging cross-section substantially orthogonal to a bloodstream path inside the heart based on the position of the aortic valve or the pulmonary valve, and cause the gantry to image the imaging cross-section of the object at the specified position of the imaging cross-section.

Hereinafter, embodiments of the present invention will be explained with reference to the accompanying drawings.

(1) Overall Structure

Figure 1:
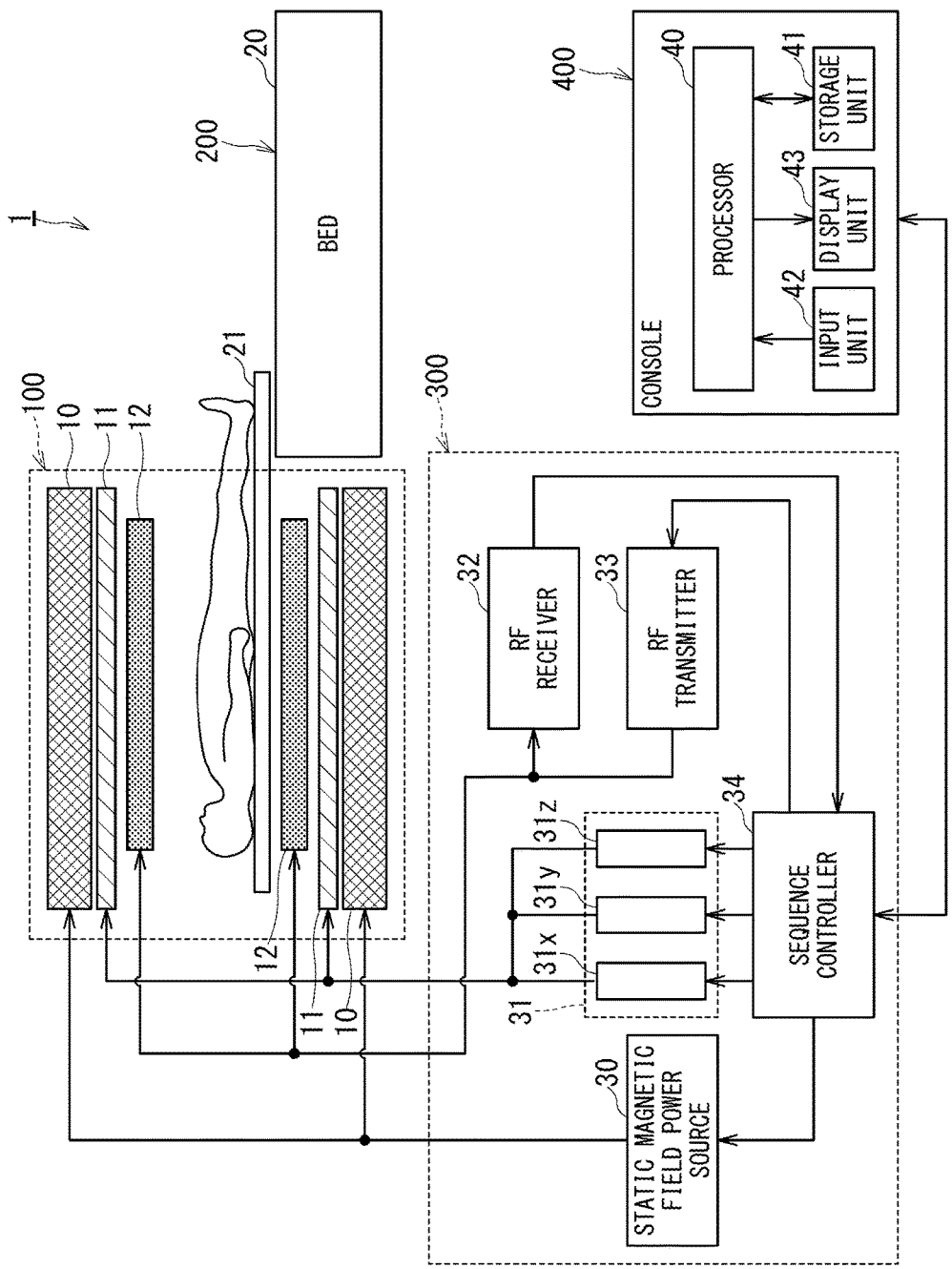
FIG. 1 is a block diagram showing an example of overall structure of a magnetic resonance apparatus.

FIG. 1 is a block diagram showing an example of overall structure of a magnetic resonance apparatus 1 of the present embodiment. The magnetic resonance apparatus 1 includes a gantry 100, a bed 200, a control cabinet 300, a console 400 and so on.

The gantry 100 includes a static field magnet 10, a gradient coil 11, an RF coil 12 and so on, and these components are included in a cylindrical housing. The bed 200 includes a bed body 20 and a table 21.

The control cabinet 300 includes a static magnetic field power source 30, a gradient magnetic field power source 31 (31x for an X axis, 31y for a Y axis and 31z for a Z axis), an RF receiver 32, an RF transmitter 33, a sequence controller 34 and so on. In addition, the console 400 is constituted as a computer including one or more processor(s) 40, one or more storage unit(s) 41, an input unit 42, a display unit 43 and so on.

The static field magnet 10 of the gantry 100 is substantially in the form of a cylinder, and generates a static magnetic field inside the bore (i.e. the space inside the cylindrical structure of the static field magnet 10) which is an imaging region of an object (patient). The static field magnet 10 includes a superconductive coil inside and the superconductive coil is cooled down to an extremely low temperature by liquid helium. The static field magnet 10 generates the static magnetic field by supplying the superconductive coil with the electric current provided from the static magnetic field power source 30 in an excitation mode. After this, the static field magnet 10 shifts to a permanent current mode and thereby the static magnetic field power source 30 is separated. Once it enters the permanent current mode, the static field magnet 10 continues to generate a strong static magnetic field for a long time, for example, over one year. Incidentally, the static field magnet 10 may be constituted as a permanent magnet.

The gradient coil 11 is also substantially in the form of a cylinder, and fixed to the inside of the static field magnet 10. This gradient coil 11 applies gradient magnetic fields to the object in the respective directions of the X axis, the Y axis and the Z axis, by using the electric currents supplied from the gradient magnetic field power sources (31x, 31y, 31z).

The bed body 20 of the bed 200 can move the table 21 in the upward and downward directions, and moves the object on the table 21 to a predetermined height before imaging. After this, in time of imaging, the bed body 20 moves the table 21 in the horizontal direction so as to move the object inside the bore.

The RF coil 12 is also called a whole body coil, and is fixed to the inside of the gradient coil 11.

The RF coil 12 transmits RF pulses supplied from the RF transmitter 33 toward the object and receives the magnetic resonance signals emitted from the object due to excitation of hydrogen atoms.

The RF transmitter 33 supplies the RF coil 12 with RF pulses on the basis of a command from the sequence controller 34. Meanwhile, the RF receiver 32 detects the magnetic resonance signals received by the RF coil 12, and transmits raw data obtained by digitizing the detected magnetic resonance signals to the sequence controller 34.

Under the control of the console 400, the sequence controller 34 performs a scan of the object by respectively driving the gradient magnetic field power source 31, the RF transmitter 33 and the RF receiver 32. Then, when the sequence controller 34 receives the raw data from the RF receiver 32 by performing the scan, the sequence controller 34 transmits the raw data to the console 400.

The console 400 controls the entirety of the magnetic resonance apparatus 1. Specifically, the console 400 receives commands and various kinds of information such as imaging conditions or the like inputted via a mouse and a keyboard (of the input unit 42) operated by a clinical examiner and so on. Then, the processor(s) 40 makes the sequence controller 34 perform a scan on the basis of the inputted imaging conditions, and reconstructs images by using the raw data transmitted from the sequence controller 34. The reconstructed images are displayed on the display unit 43 or stored in the storage unit(s) 41.

The magnetic resonance apparatus 1 sets the aforementioned cross-sections appropriate for the kinetic observation of the valves and cross-sections appropriate for understanding cardiac hemodynamics. More specifically, the magnetic resonance apparatus 1 performs processing of setting transverse sections of valves inside the heart and transverse sections of main blood flow paths inside the heart. Hereinafter, this processing is referred to as automatic processing of setting imaging cross-sections of valves The automatic processing of setting imaging cross-sections of valves is mainly performed by the console 400.

Incidentally, in the present embodiment shown below, an example in which imaging cross-sections are selected (set) without operation by an operator will be explained. However, the magnetic resonance apparatus 1 may be constituted so as to receive a command to set imaging cross-sections, a command to correct imaging cross-sections selected by the magnetic resonance apparatus 1.

Figure 2:
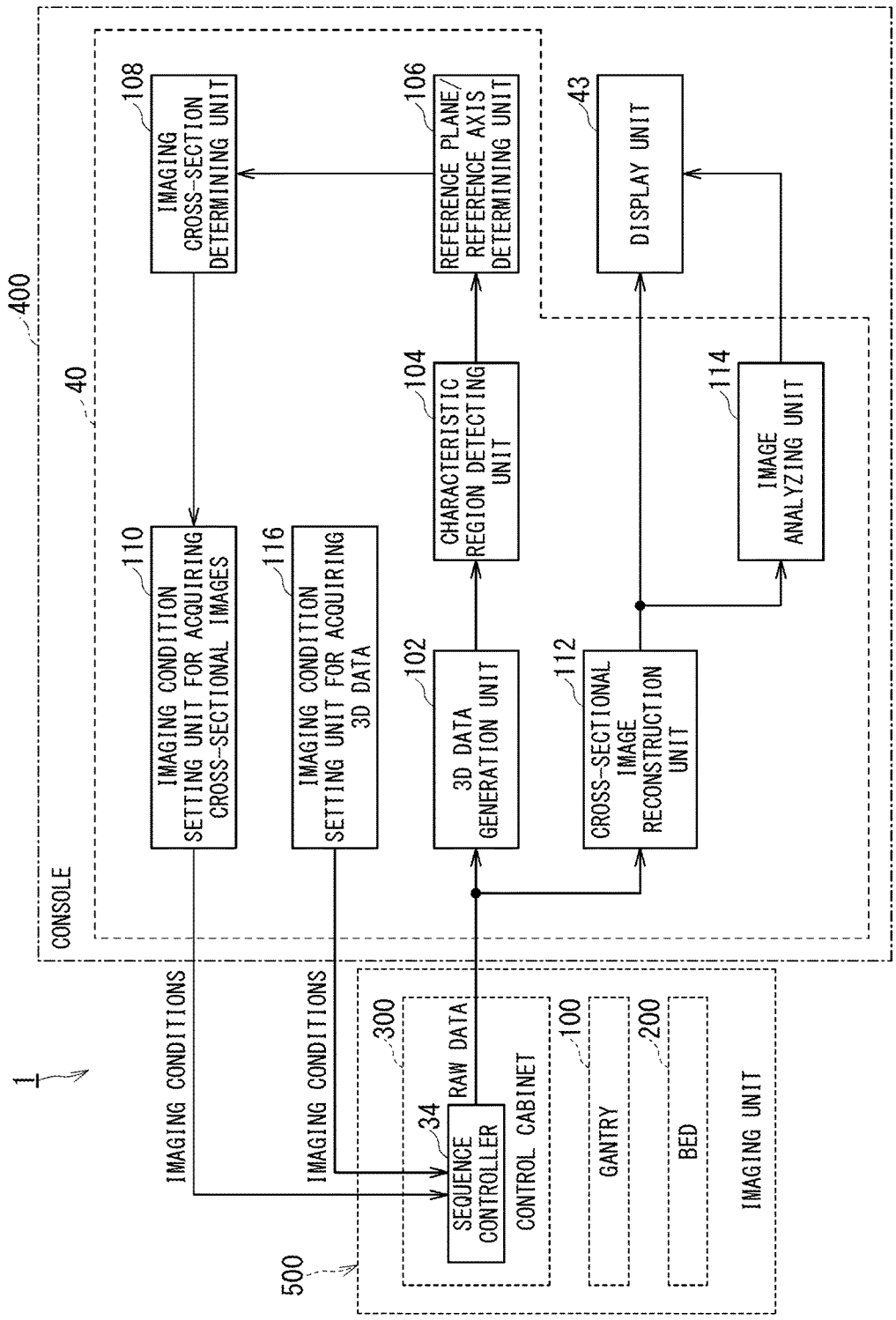
FIG. 2 is a block diagram showing components relevant to the automatic processing of setting imaging cross-sections of valves.

FIG. 2 is a block diagram showing components relevant to the automatic processing of setting imaging cross-sections of valves. As shown in FIG. 2, the magnetic resonance apparatus 1 includes units such as an imaging condition setting unit 116 for acquiring 3D (three-dimensional) data, a 3D data generation unit 102, a characteristic region detecting unit 104 (detecting unit 104), a reference plane/reference axis determining unit 106, an imaging cross-section determining unit 108 (specifying unit 108), an imaging condition setting unit 110 for acquiring cross-sectional images, a cross-sectional image reconstruction unit 112, an image analyzing unit 114.

The function of each of these units (116, 102, 104, 106, 108, 110, 112, 114) is achieved by processing circuitry such as the processor(s) 40 of the console 400 which executes predetermined computer-executable instructions stored in one or more memories such as the storage unit(s) 41. However, it is not limited to such software processing. For example, the function of each of these units may be achieved by hardware processing with the use of ASIC and so on. Alternatively, it may be achieved by combination of the software processing and the hardware processing.

Out of the above respective units, the imaging condition setting unit 116 for acquiring 3D data sets imaging conditions for performing imaging of multi-slice axial cross-sections on the sequence controller 34, in order to acquire three-dimensional data. The sequence controller 34 performs imaging of multi-slice axial cross-sections in accordance with these imaging conditions. The 3D data generation unit 102 acquires the magnetic resonance signals from the object obtained by this imaging, and generates the three-dimensional data including the heart of the object by using the acquired magnetic resonance signals.

The characteristic region detecting unit 104 detects positions of a plurality of anatomically characteristic regions inside the heart such as the mitral valve, the aortic valve, the left ventricular apex (i.e., the cardiac apex) from the acquired three-dimensional data.

The reference plane/reference axis determining unit 106 and the imaging cross-section determining unit 108 determines reference planes such as the three-chamber long axis plane and the central axis (reference axis) of a duct of a bloodstream path such as the aortic duct from the detected positions of the plurality of anatomically characteristic regions. The reference plane/reference axis determining unit 106 and the imaging cross-section determining unit 108 also identifies (specifies) a cross-section, which is substantially orthogonal to the blood flow route inside the heart (i.e. the central axis of a duct of a bloodstream path) and includes a predetermined observation region inside the heart such as the aortic valve or its adjacent region, as the imaging cross-section. Details of determining the imaging cross-sections will be described below.

Information designating a specified observation region (for example, information that the observation region is the aortic valve) is inputted into the magnetic resonance apparatus 1 via the input unit 42. On the basis of this information, the reference plane/reference axis determining unit 106 determines the reference plane (three-chamber long axis plane) and the central axis of the aortic duct, which are needed to determine the imaging cross-section suitable for the kinetic observation of the aortic valve. In addition, the characteristic region detecting unit 104 similarly detects positions of the plurality of anatomically characteristic regions (the mitral valve, the aortic valve and the left ventricular apex) needed to determine the three-chamber long axis plane, based on the information designating a specified observation region (for example, information that the observation region is the aortic valve).

The imaging condition setting unit 110 for acquiring cross-sectional images sets imaging conditions based on the determined imaging cross-sections and the imaging method of the cross-sections (for example, cine imaging with the use of a SSFP (Steady State Free Precision) technique and a PC (Phase Contrast) technique), on the sequence controller 34.

The sequence controller 34 performs imaging of the imaging cross-sections on the basis of these imaging conditions. The cross-sectional image reconstruction unit 112 reconstructs cross-sectional images by using the magnetic resonance signals (raw data) obtained by this imaging, and display them on the display unit 43.

The image analyzing unit 114 analyzes cardiac hemodynamics including analysis of blood flow amount, on the basis of blood flow velocity information included in the reconstructed cross-sectional images, information on radius sizes of respective bloodstream ducts and so on.

Incidentally, as shown in the left side of FIG. 2, the entirety of the components of the magnetic resonance apparatus 1 excluding the console 400 is defined as an imaging unit 500.

(2) Operation

Details of the operation of the magnetic resonance apparatus 1 constituted as above are explained as follows.

Figure 3:
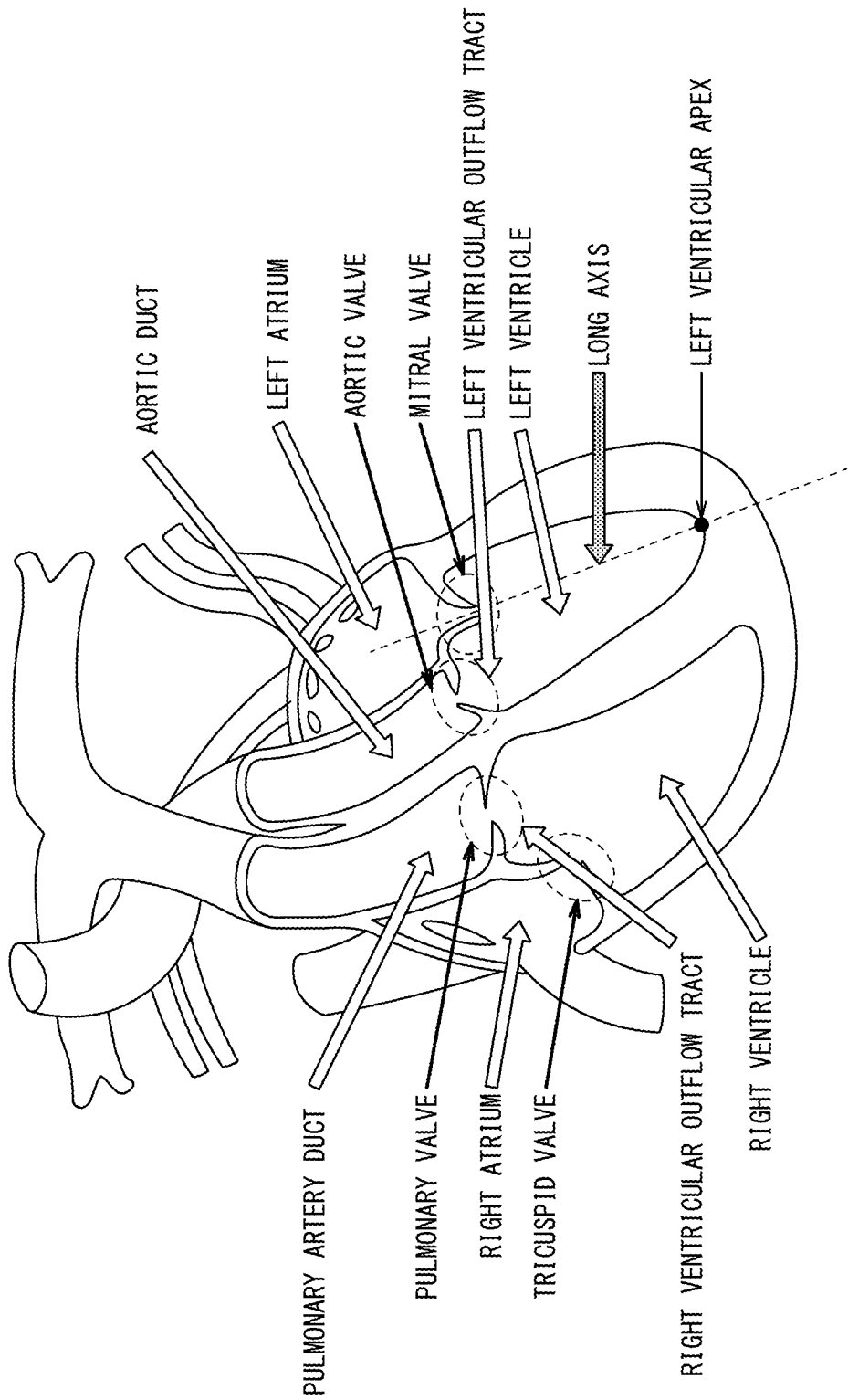
FIG. 3 illustrates an anatomical heart model which is the imaging target.

FIG. 3 is a diagram illustrating an anatomical heart model which is the imaging target of the magnetic resonance apparatus 1 of the present embodiment.

As is well known, in the systole, blood carried from the left ventricle flows through the aortic valve by way of the left ventricular outflow tract to reach the aortic duct, and then is carried to the respective intracorporeal arteries. Additionally, in the systole, venous blood carried from the right ventricle flows through the pulmonary valve by way of the right ventricular outflow tract to reach the pulmonary artery duct, and then is carried to the bilateral lungs.

On the other hand, in the diastole, arterial blood returned from the bilateral lungs flows into the left atrium, and then flows into the left ventricle by way of the mitral valve. In addition, venous blood returned from the respective intracorporeal veins flows into the right atrium, and then flows into the right ventricle by way of the tricuspid valve.

Incidentally, the bloodstream path, which is adjacent to the mitral valve and flows from the left atrium into the left ventricle, is referred to as a left ventricular inflow tract, for the sake of convenience. In addition, the bloodstream path, which is adjacent to the tricuspid valve and flows from the right atrium into the right ventricle, is referred to as a right ventricular inflow tract. Moreover, the aortic duct, the pulmonary artery duct, the left ventricular inflow tract and the right ventricular inflow tract are collectively referred to as a bloodstream duct, in a simple term. In addition, the axis connecting the bottom end of the left ventricle (left ventricular apex) with the center of the mitral valve is referred to as a left ventricular long axis or a long axis in a simple term.

Figure 4:
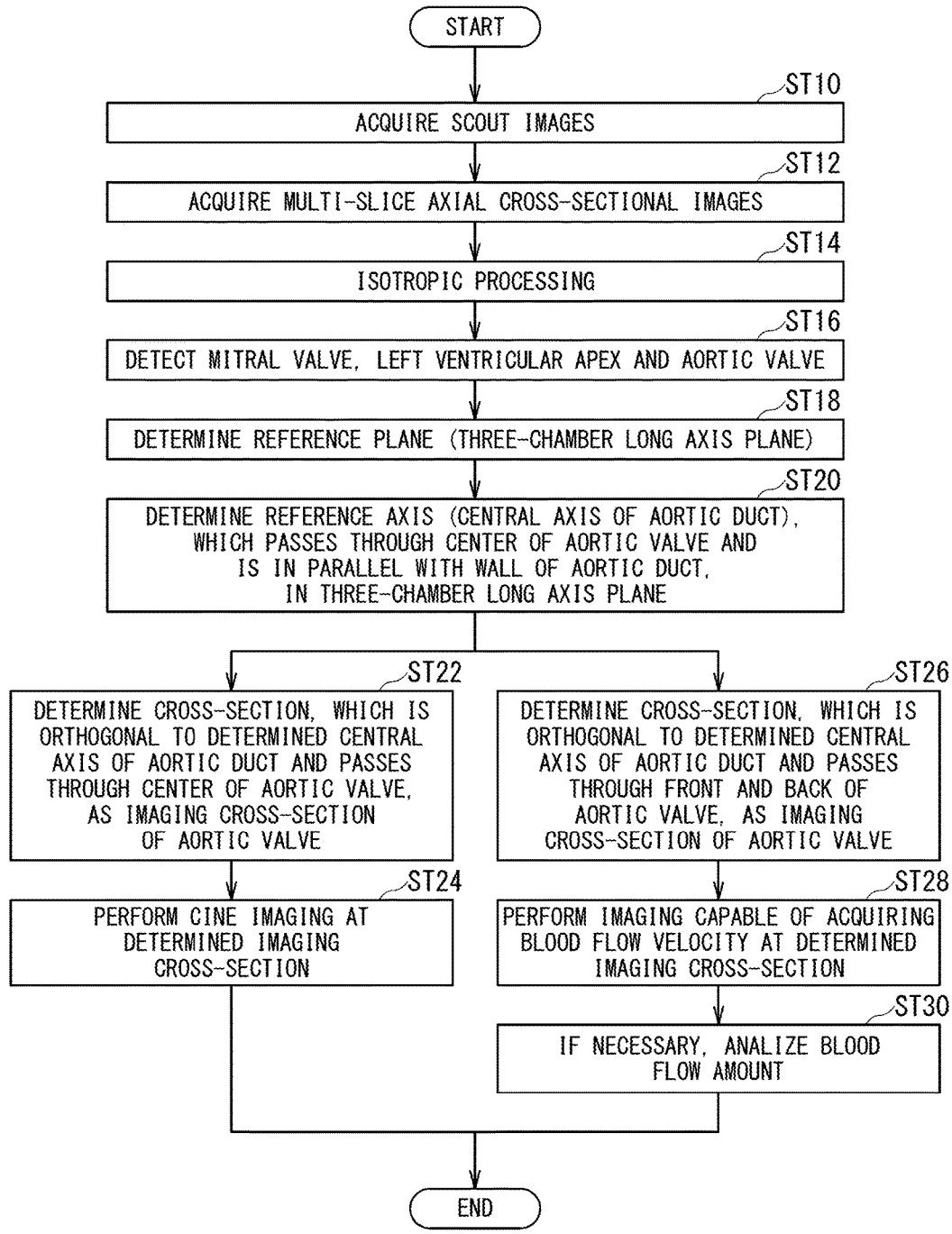
FIG. 4 is a flowchart showing an example of the automatic processing of setting imaging cross-sections of valves and imaging processing for the automatically determined imaging cross-sections.

FIG. 4 is a flowchart showing an example of the automatic processing of setting imaging cross-sections of valves and imaging processing for the determined imaging cross-sections performed by the magnetic resonance apparatus 1.

Although the magnetic resonance apparatus 1 can select any valve and any bloodstream duct inside the heart, an example in which the aortic valve and the aortic duct connecting to the aortic valve are selected as imaging targets will be explained below. Incidentally, it is assumed that an operator preliminarily inputs information that the imaging targets (observation regions) are the aortic valve and the aortic duct connecting to this via the input unit 42.

First, in the step ST10, data for scout images including the heart of the object are acquired, and the scout images are generated. The scout images are, for example, three cross-sectional images: an axial cross-sectional image, a coronal cross-sectional image and a sagittal cross-sectional image. These scout images are displayed on the display unit 43. An operator determines a three-dimensional FOV (Field of View) covering the entirety of the heart, with reference to the scout images displayed on the display unit 43. Then, the operator sets imaging conditions for imaging a plurality of slices (multi-slice) of axial cross-sectional images covering the entirety of the heart on the imaging condition setting unit 116 for acquiring 3D data, via the input unit 42.

Imaging of the object is performed in accordance with these imaging conditions, and thereby multi-slice axial cross-sectional images covering the entirety of the heart, i.e. three-dimensional cardiac data are acquired (in the step ST12).

Figure 5:
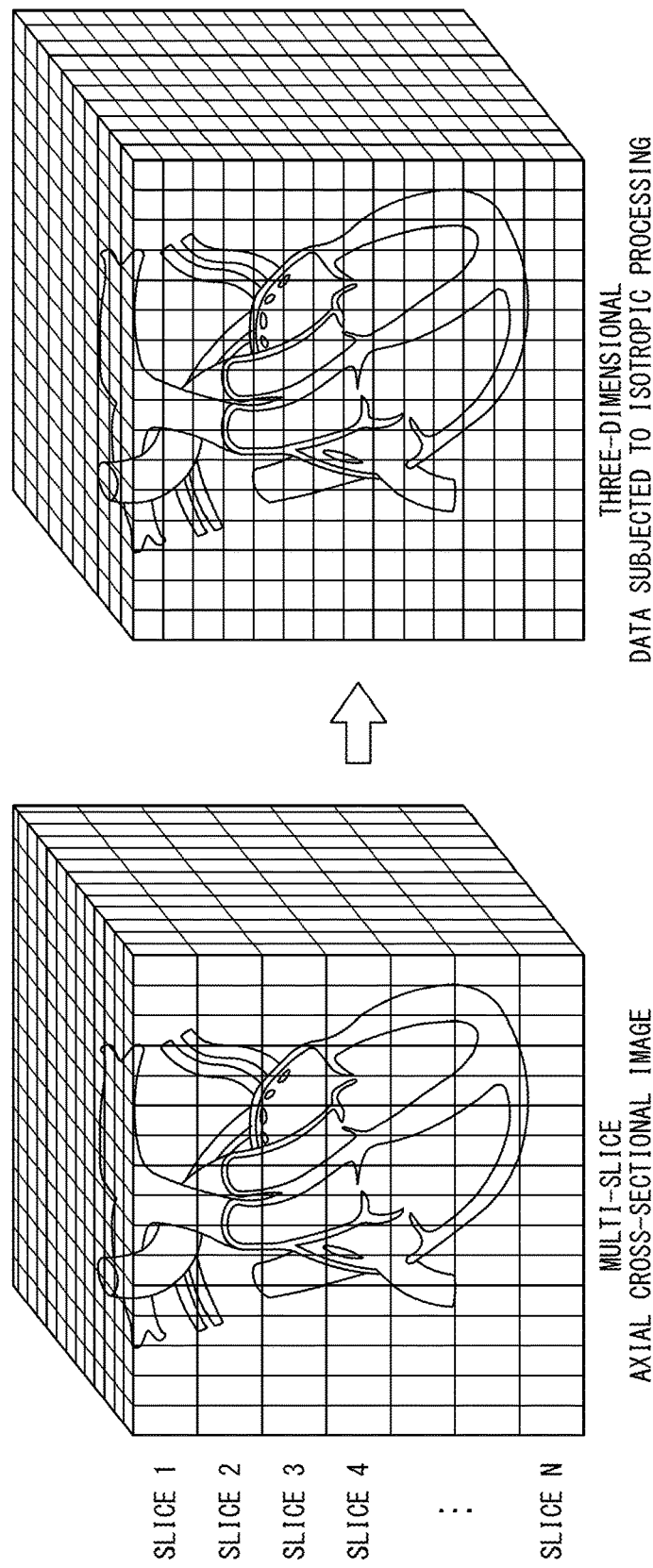
FIG. 5 is a chart showing multi-slice axial cross-sectional images (three-dimensional data) and isotropic processing.

The left side of FIG. 5 is a chart indicating the acquired multi-slice axial cross-sectional images (three-dimensional data). When the resolution of the axial cross-sections is different from the resolution given by the slice interval of these axial cross-sections, isotropic processing with the use of interpolation processing or the like is performed so as to uniformize the intervals between the respective voxels and thereby isotropic three-dimensional data are generated as shown in the right side of FIG. 5 (in the step ST14).

Next, in the step ST16, the characteristic region detecting unit 104 detects positions of at least three anatomically characteristic regions inside the heart from the three-dimensional data generated in the step ST14.

More specifically, when the observation regions are the aortic valve and the aortic duct connecting to this, the characteristic region detecting unit 104 detects the respective positions of the mitral valve, the left ventricular apex and the aortic valve from the three-dimensional data. In the positional detection of them, for example, a method based on a machine learning technique described in "Automatic slice alignment method for cardiac magnetic resonance imaging", Magn Reson Mater Phy DOI: 10.1007/s10334-012-0361-4, by S. Nitta, T. Taguchi, N. Matsumoto, S. Kuhara, K. Yokoyama, R. Ishimura, T. Nitatori, (2013) may be used. Alternatively, a template matching method may be used.

Instead of the method based on the machine learning technique or in addition to this, the positional detection of the anatomically characteristic regions may be performed by using a template matching method. For example, accuracy of the positional detection may be improved by (a) detecting the respective center positions of the mitral valve, the left ventricular apex and the aortic valve under the method based on the machine learning technique and then (b) performing the template matching on the regions adjacent to the detected center positions.

In the step ST18 of FIG. 4, based on the determined positions of the three anatomically characteristic regions (the mitral valve, the left ventricular apex and the aortic valve), the reference plane passing through these three positions is determined.

Figure 6:
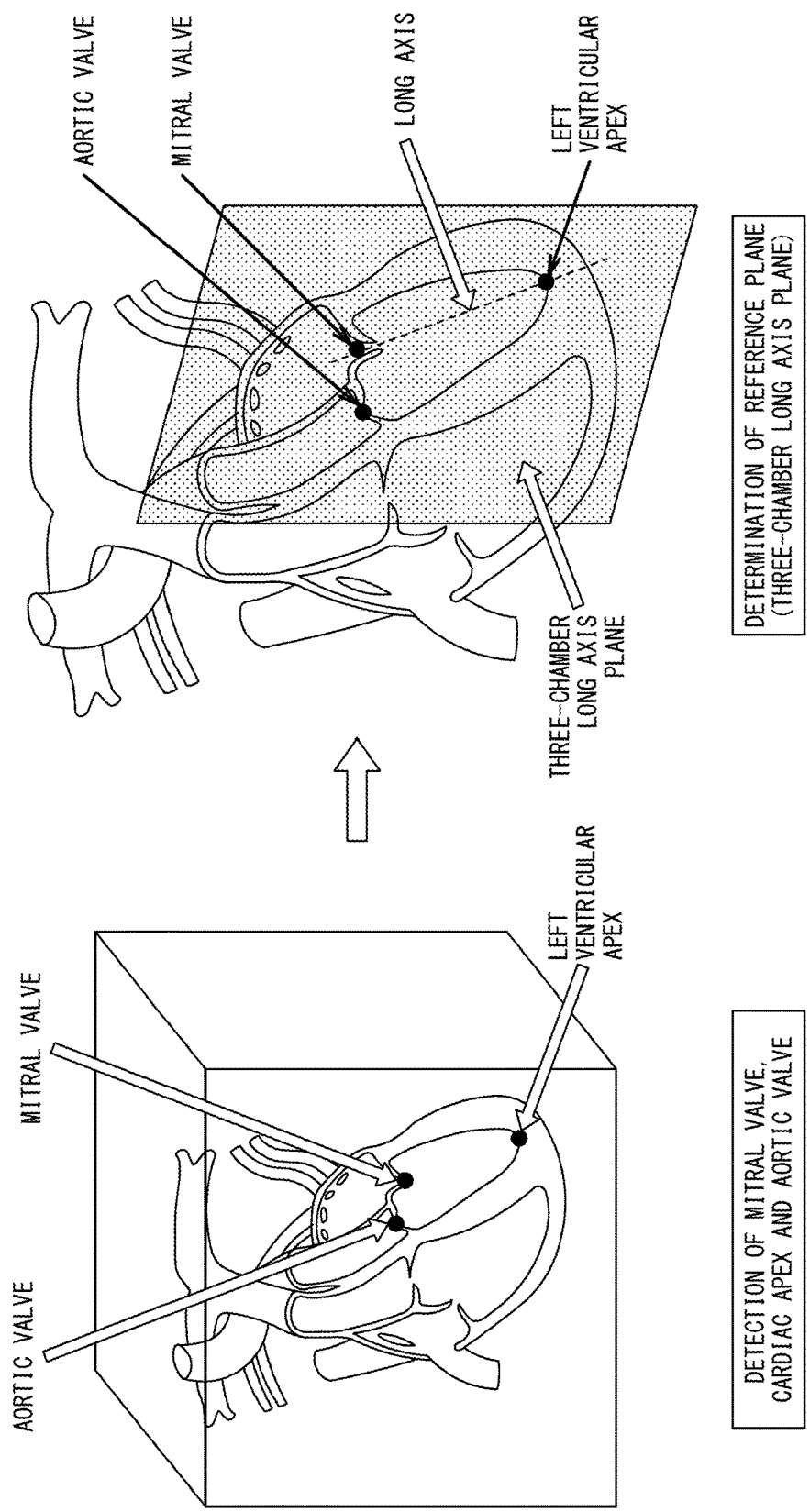
FIG. 6 is a chart explaining a method of determining the reference plane (three-chamber long axis plane) by using positions of three anatomically characteristic regions.

As shown in the left part of FIG. 6, if the respective center positions of the mitral valve, the left ventricular apex and the aortic valve are determined in the step ST16, the cross-section passing through these three positions can be determined (in the step ST18; see the right part of FIG. 6). Because an imaged picture of the cross-section passing through the respective center positions of the mitral valve, the left ventricular apex and the aortic valve can satisfactorily depict the left ventricle, the left atrium and the left ventricular outflow tract, it is called a three-chamber long axis plane (or three-chamber plane). The three-chamber long axis plane is a cross-section which includes the long axis and passes through the center of the aortic valve.

Conventionally, in order to determine the three-chamber long axis plane, the position of the vertical long axis plane is determined from multi-slice axial cross-sectional images (three-dimensional data), then the position of the horizontal long axis plane is determined from the vertical long axis view imaged at the determined position of the vertical long axis plane, then the position of the short axis plane is determined from the horizontal long axis view imaged at the determined position of the horizontal long axis plane, and the chain oblique technique is sequentially continued in this manner so as to determine the three-chamber long axis plane in its final phase.

Therefore, in the conventional technology, errors are accumulated because the positional error of the previously determined cross-section influences the position of the subsequently determined cross-section, and accordingly wide experience and highly advanced skills in positioning operation have been required for an operator in order to secure accuracy of setting the position of the three-chamber long axis plane.

In contrast, in the present embodiment, the three center positions of the mitral valve, the left ventricular apex and the aortic valve are automatically detected and the three-chamber long axis plane can be determined directly from these three positions. Therefore, determination of the three-chamber long axis plane can be performed in an extremely short time and the three-chamber long axis plane can be determined with high positional accuracy, without relying on highly advanced skills of an operator.

Next, in the step ST20 of FIG. 4, an axis, which is substantially in parallel with the wall surface of the aortic duct and passes through the center of the aortic valve in the three-chamber long axis plane determined in the above manner, is determined as the reference axis. This reference axis is equal to the central axis of the aortic duct.

Figure 7:
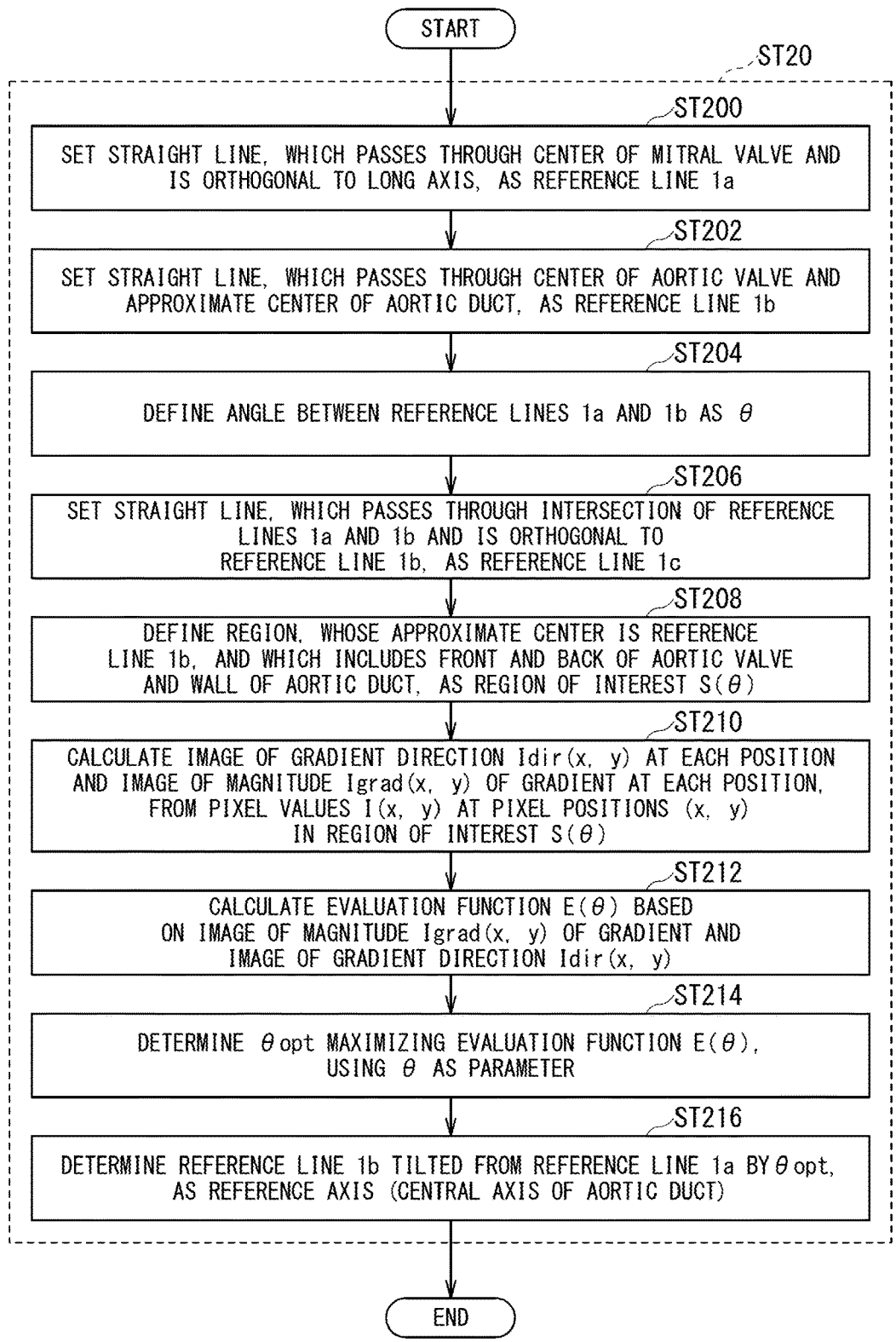
FIG. 7 is a flowchart showing an example of the concrete processing of determining the reference axis (central axis of the aortic duct)
Figure 8:
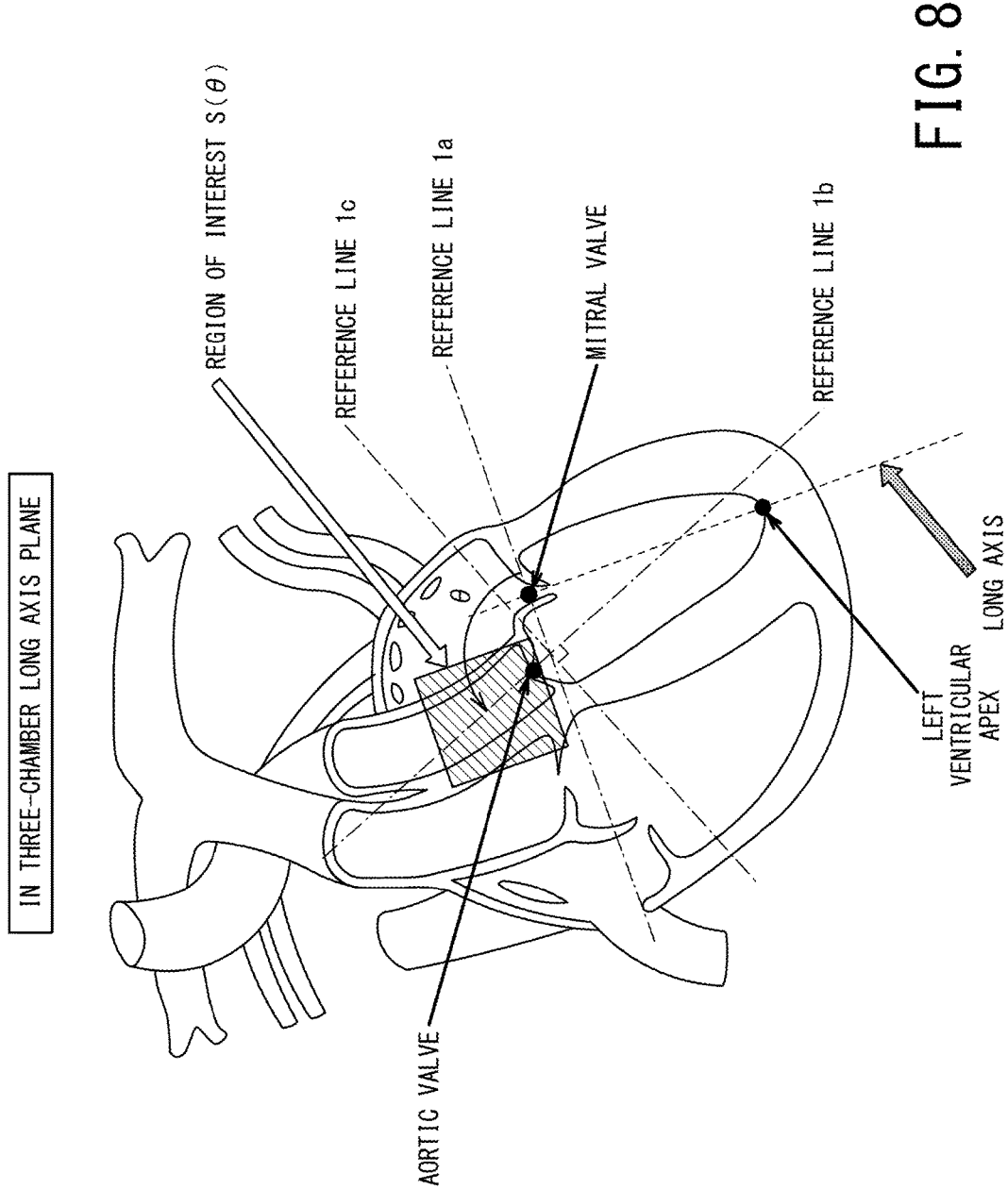
FIG. 8 is the first explanatory diagram showing a method of determining the reference axis (central axis of the aortic duct)
Figure 9:
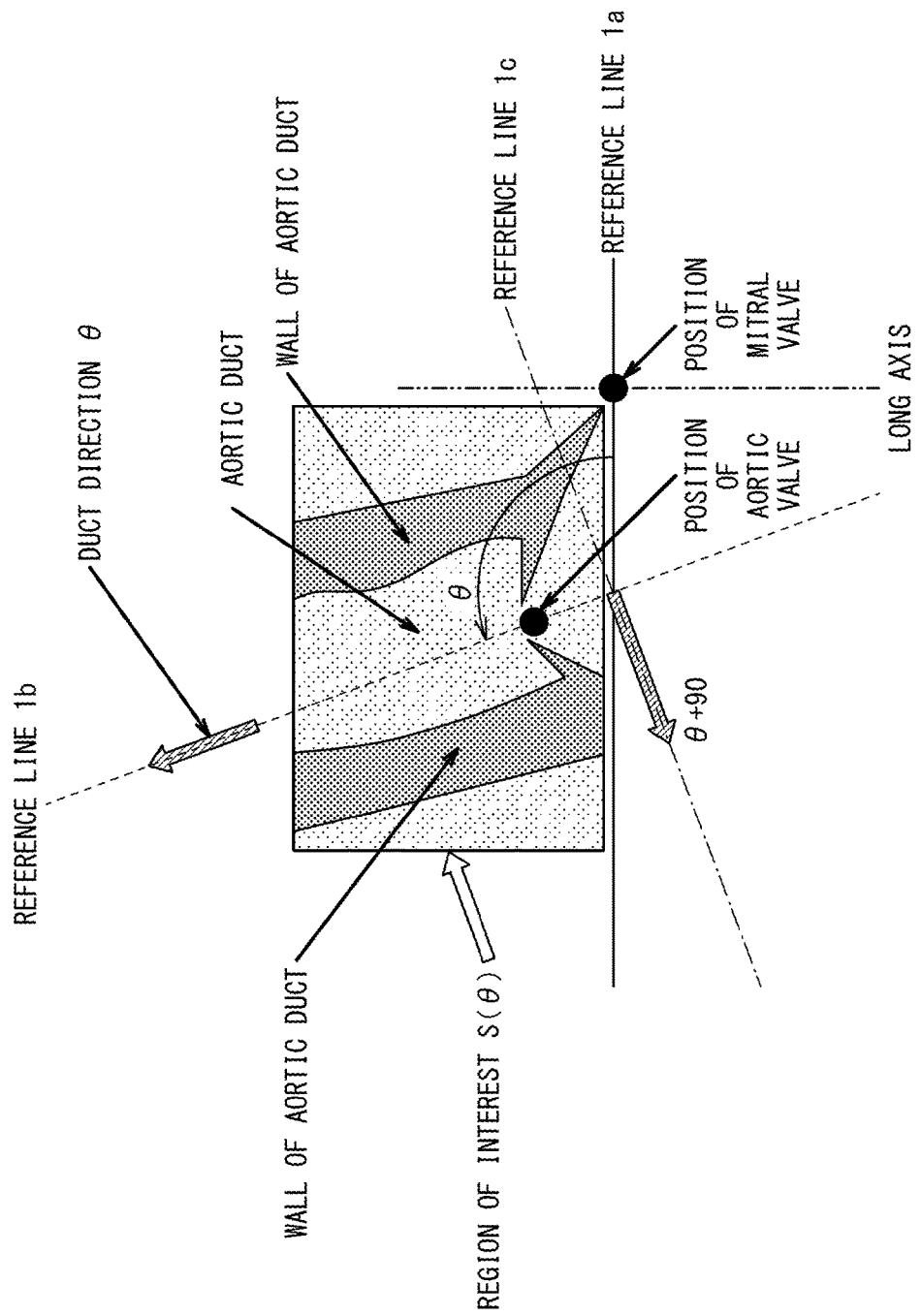
FIG. 9 is the second explanatory diagram showing a method of determining the reference axis (central axis of the aortic duct)
Figure 10A:
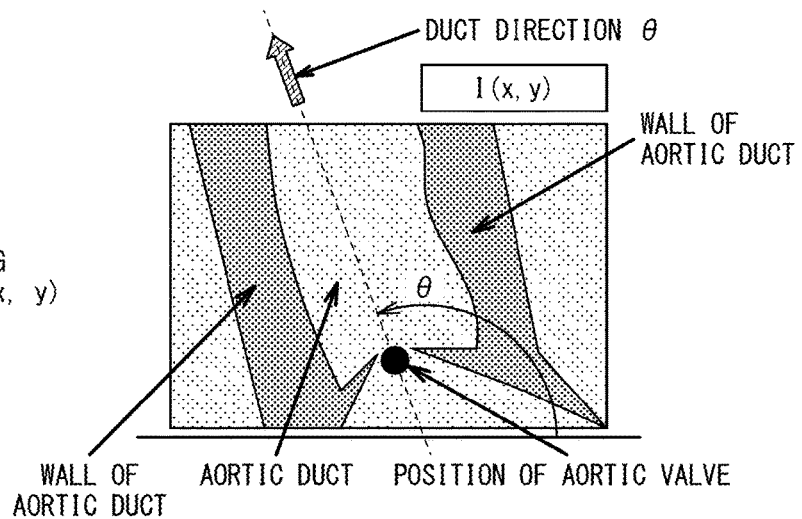
FIG. 10A is the third explanatory diagram showing a method of determining the reference axis (central axis of the aortic duct) by using an image indicating the pixel value I(x, y) at each of the pixel positions (x, y) in the region of interest S(θ)
Figure 10B:
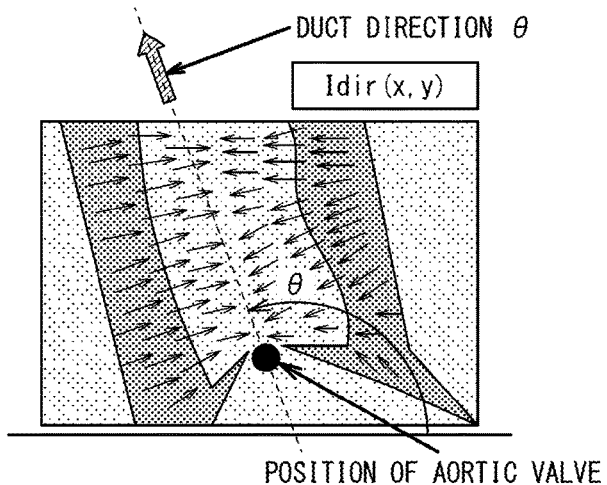
FIG. 10B is a diagram showing an example of an image indicating the gradient direction Idir(x, y) of the pixel value I(x, y) at each of the pixel positions (x, y) obtained by a subsequent process after FIG. 10(a)
Figure 10C:
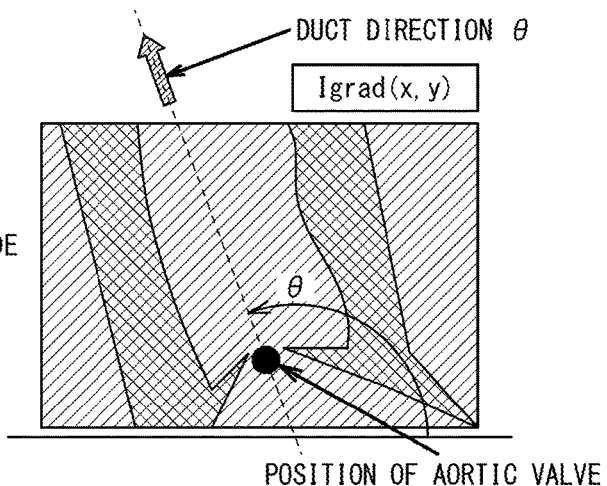
FIG. 10C is a diagram showing an example of an image indicating the magnitude Igrad(x, y) of the gradient of each of the pixel values I(x, y) obtained by a subsequent process after FIG. 10(b)

FIG. 7 is a detailed flowchart showing the processing of the step ST20 in FIG. 4 with a more detailed example. The detailed example of determining the reference axis (central axis of the aortic duct) in the three-chamber long axis plane will be explained with reference to the flowchart of FIG. 7 and FIG. 8 to FIG. 11. Each of the following steps is processing within the three-chamber long axis plane. In addition, FIG. 9 is a chart obtained by schematically magnifying the vicinity of the later-described region of interest S(θ) in FIG. 8.

First, a straight line, which passes through the center of the mitral valve and is orthogonal to the long axis, is set as a reference line 1$a$ (in the step ST200). The reference line 1$a$ is required to merely become orthogonal to the long axis in the three-chamber long axis plane, and it does not necessarily need to pass through the center of the mitral valve. However, the straight line, which passes through the center of the mitral valve and is orthogonal to the long axis, is explained as the reference line 1$a$ in the following.

Next, a straight line, which passes through the center of the aortic valve and the approximate center of the aortic duct, is set as a reference line 1*b* (in the step ST202). Then, the angle between the reference line 1*a* and the reference line 1*b* is defined as θ(deg), in the step ST204. The reference line 1*b* at this phase is not perfectly the center of the duct but may be a straight line passing through an approximate center of the duct. In addition, the angle θ is a parameter to be determined to be an optimum value by being subjected to processing of the following steps, and the initial value of the angle θ can be preliminarily selected on the basis of the average value obtained from data of the past medical cases Next, a straight line, which passes through the intersection of the reference line 1*a* and the reference line 1*b* and is orthogonal to the reference line 1*b*, is defined as a reference line 1*c* (in the step ST206). Incidentally, setting of the reference line 1*c* may be omitted.

Next, the region, whose approximate center is the reference line 1*b* and which includes the front and back of the aortic valve and the wall of the aortic duct, is defined as a region of interest S(θ) (in the step ST208). The position, the size or the like of the region of interest S(θ) may be preliminarily set based on the average value, standard deviation and so on obtained from data of many medical cases. The region of interest S(θ) is determined so as to become a small region including the area of the aortic duct out of the entire cardiac region.

Next, on the basis of the image (FIG. 10A) indicating the pixel value I(x, y) at each of the pixel positions (x, y) in the region of interest S(θ), an image (FIG. 10B) of a gradient direction Idir(x, y) which indicates a direction of a gradient of the pixel value I(x, y) at each of the pixel positions (x, y), and further, an image (FIG. 10C)) of a gradient magnitude Igrad(x, y) which indicates a magnitude of the gradient of the pixel value I(x, y) at each of the pixel positions (x, y) are calculated in the step ST210. In other words, if the gradient of the pixel value I(x, y) at each of the pixel positions(x, y) is expressed by a vector, the direction (angle (deg)) of this vector is equal to the gradient direction Idir(x, y) and the magnitude of this vector is equal to the magnitude Igrad(x, y) of the gradient. These are calculated in the step ST210.

Figure 11:
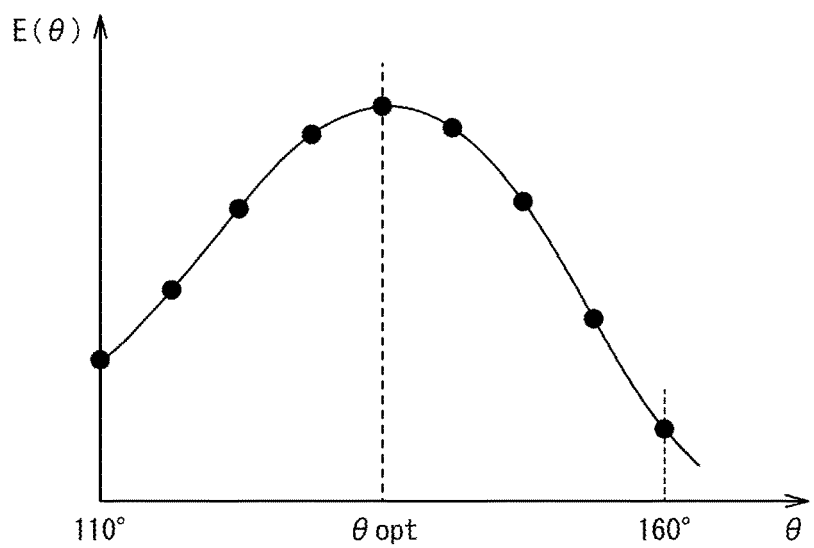
FIG. 11 is the fourth explanatory diagram showing a method of determining the reference axis (central axis of the aortic duct)

Next, on the basis of the image indicating the gradient direction Idir(x, y) and the image indicating the magnitude Igrad(x, y) of the gradient, for example, the evaluation function E(θ) expressed by the following equation (1) is calculated in the step ST212 of FIG. 7 (see FIG. 11).

$$E(\theta)=\Sigma I\text{grad}(x, y)*[\cos \{2*(I\text{dir}(x, y)-(\theta+90°))\}] \quad \text{equation (1)}$$

In the equation (1), a function f(x, y, θ) expressed by [cos {2*(Idir(x, y)−(θ+90°))}] is a function that reaches the maximum value "1" when the direction of duct axis θ is orthogonal to the gradient direction Idir(x, y). In addition, the evaluation function E(θ) is obtained by, first, weighting the function f(x, y, θ) with the gradient magnitude I grad(x, y) per pixel position (x, y), and then, taking the summation of the weighted function within the region of interest S(θ).

As shown in the bottom part of FIG. 11, this evaluation function E(θ) takes the maximum value under the condition where the direction of duct axis θ is orthogonal to the gradient direction of each of the pixel values within the region of interest S(θ) (in particular, the gradient direction of each of the pixel value in the vicinity of the mutually adjacent area between the duct wall and blood), when viewing the duct inside the region of interest S(θ) as a whole.

The direction θ at which the evaluation function E(θ) reach the maximum value is the optimal direction of duct axis θopt. In other words, such a direction of duct axis θ that can be regarded as parallel with the direction along the duct wall as a whole can be determined as the optimal direction of duct axis θopt (in the step ST214).

Specifically, the optimal direction of duct axis θopt maximizing the evaluation function E(θ) is determined by repeating the processing of the step ST204 to the step ST212 with the use of the direction of duct axis θ as a parameter.

On the basis of the optimal direction of duct axis θopt determined in the above manner, the central axis of the aortic duct (i.e. the reference axis which passes through the center of the aortic valve and is substantially in parallel with the wall surface of the aortic duct) can be determined in the step ST216.

Incidentally, the aforementioned processing of the step ST18 and the step ST20 in FIG. 4 and the step ST200 to the step ST216 in FIG. 7 is performed by the reference plane/reference axis determining unit 106 shown in FIG. 2.

Figure 12B:
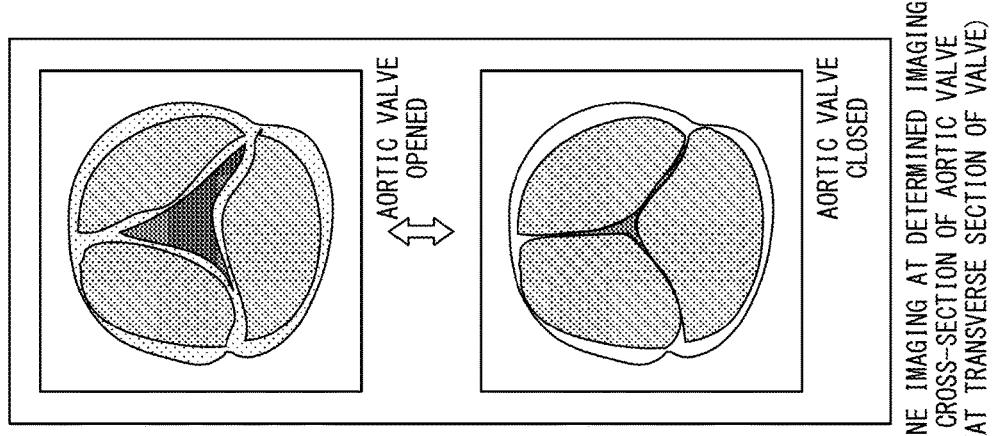
FIG. 12B is a chart showing an example of a dynamic image obtained by performing cine imaging on the imaging cross-section determined by the method of FIG. 12A.
Figure 12A:
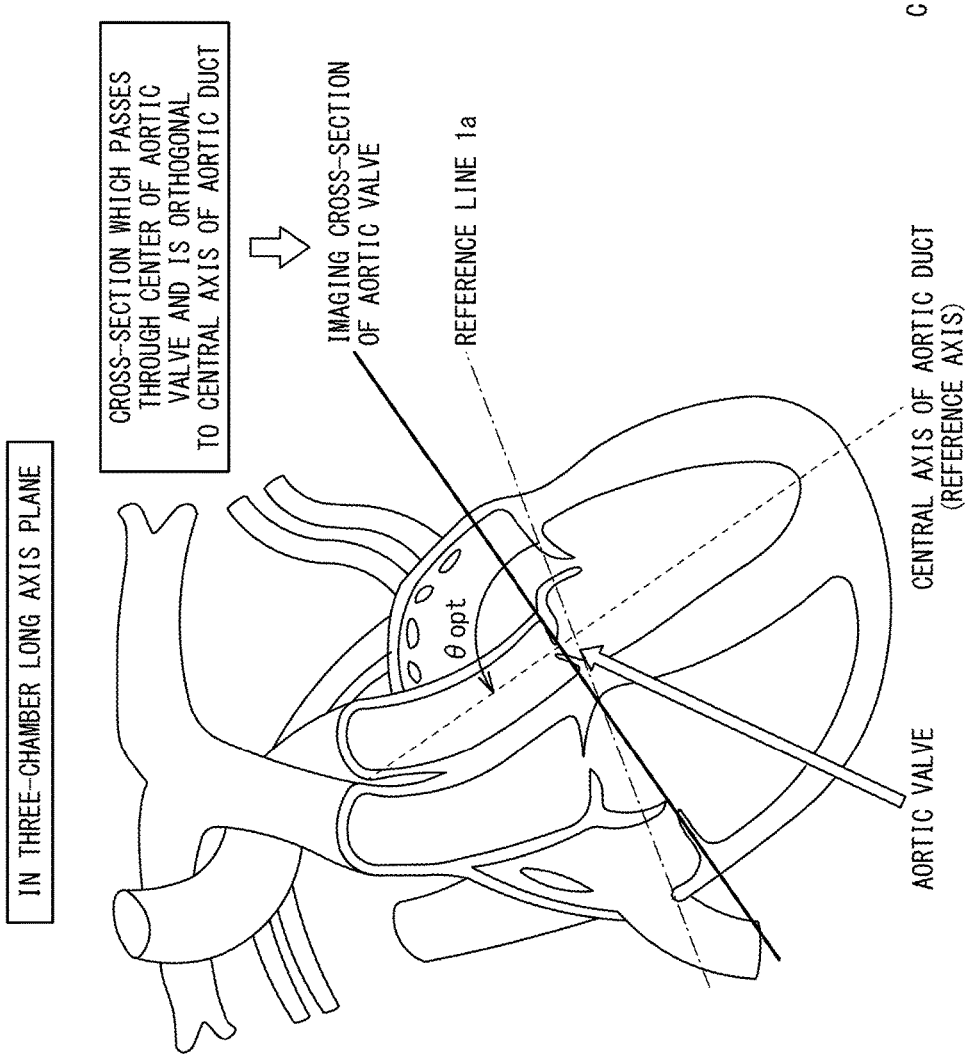
FIG. 12A is a chart showing an example of a method of determining the imaging cross-section of the aortic duct.

Returning to FIG. 4, in the next step ST22, a cross-section, which is orthogonal to the determined reference axis (central axis of the aortic duct) and passes through the central position of the aortic valve, is determined as a imaging cross-section of the aortic valve, as shown in FIG. 12(*a*). The processing of step ST22 is performed by the imaging cross-section determining unit 108 shown in FIG. 2. The imaging cross-section of the aortic valve determined in the above manner can precisely depict the shape and its dynamic change of the aortic valve as a picture imaged not from an oblique angle but from the front angle, because this imaging cross-section passes through the central position of the aortic valve and is in parallel with a transverse section of the aortic valve (i.e. a cross-section orthogonal to the aortic duct).

Incidentally, the imaging cross-section of the aortic valve does not necessarily need to be accurately orthogonal to the reference axis (central axis of the aortic duct), but they may be substantially orthogonal to each other. In other words, they may slightly deviate from the perfect orthogonality to the extent that is allowable when diagnosing the shape and dynamic change of the aortic valve.

The positional information of the imaging cross-section of the aortic valve determined by the imaging cross-section determining unit 108 is transmitted to the imaging condition setting unit 110 for acquiring cross-sectional images in FIG. 2. Imaging conditions such as an imaging method of the aortic valve, imaging parameters, in addition to the above positional information of the imaging cross-section of the aortic valve are inputted to the imaging condition setting unit 110 for acquiring cross-sectional images. These imaging conditions are transmitted to the sequence controller 34, and imaging of the aortic valve is performed (in the step ST24).

As to the imaging method for the aortic valve, it is not limited to a specified method but various types of imaging methods including imaging methods for still images and imaging methods for moving pictures can be used. When a fast imaging method of FE (Field Echo) type or a cine imaging method under SSFP (Steady State Free Precession) technique is performed for the aortic valve, useful information not only on diagnosis relevant to the shape of the aortic valve but also on the function of the aortic valve can be obtained. This is because the dynamic behavior of the aorta can be precisely observed from a direction perpendicular to the aortic valve, as schematically illustrated in FIG. 12B.

In the above explanation, a cross-section passing the center of the aortic valve is determined as the imaging cross-section. However, one or a plurality of cross-sections, that are orthogonal to the central axis of the aortic duct and are slightly separated from, in the central axis of the aortic duct direction, the center of the aortic valve in the vicinity of the aortic valve, may be further determined as the imaging cross-sections. As to how far the imaging cross-section to be determined is separated from the center of the aortic valve, it may be determined on the basis of data of many past medical cases.

The step ST22 and ST24 in FIG. 4 are steps for determining the imaging cross-section for imaging the aortic valve itself and imaging it.

In contrast, the step ST26 and ST28 are steps for determining the imaging cross-section for imaging the transverse section of the left ventricular outflow tract or the aortic duct connected to the aortic valve and imaging it.

In the step ST26, the imaging cross-section determining unit 108 determines the cross-section, which is orthogonal to the reference axis (central axis of the aortic duct) determined in the step ST20 and passes through at least one position of the front side and the back side of the aortic valve, as the imaging cross-section of the aortic duct or the left ventricular outflow tract. As illustrated in FIG. 13A, one cross-section at the downstream side of the aortic valve may be determined as the imaging cross-section. Alternatively, one cross-section at the upstream side of the aortic valve may be determined as the imaging cross-section. Further alternatively, both cross-sections at the upstream side and the downstream side of the aortic valve or a plurality of cross-sections including both the upstream side and the downstream side of the aortic valve may be determined as the imaging cross-sections.

Then, in the step ST28, the transverse section of the aortic duct or the left ventricular outflow tract is imaged at the determined imaging cross-section. As to imaging methods of these transverse sections, for example, an imaging method capable of acquiring blood flow velocity information such as a PC (Phase Contrast) technique can be used. The positional information of the imaging cross-section(s) of the aortic duct or the left ventricular outflow tract determined by the imaging cross-section determining unit 108 is transmitted to the imaging condition setting unit 110 for acquiring cross-sectional images, and further transmitted to the sequence controller 34 together with the imaging conditions related to the imaging method such as the PC technique or the like, and then imaging of transverse sections of the aortic duct is performed.

Figure 13B:
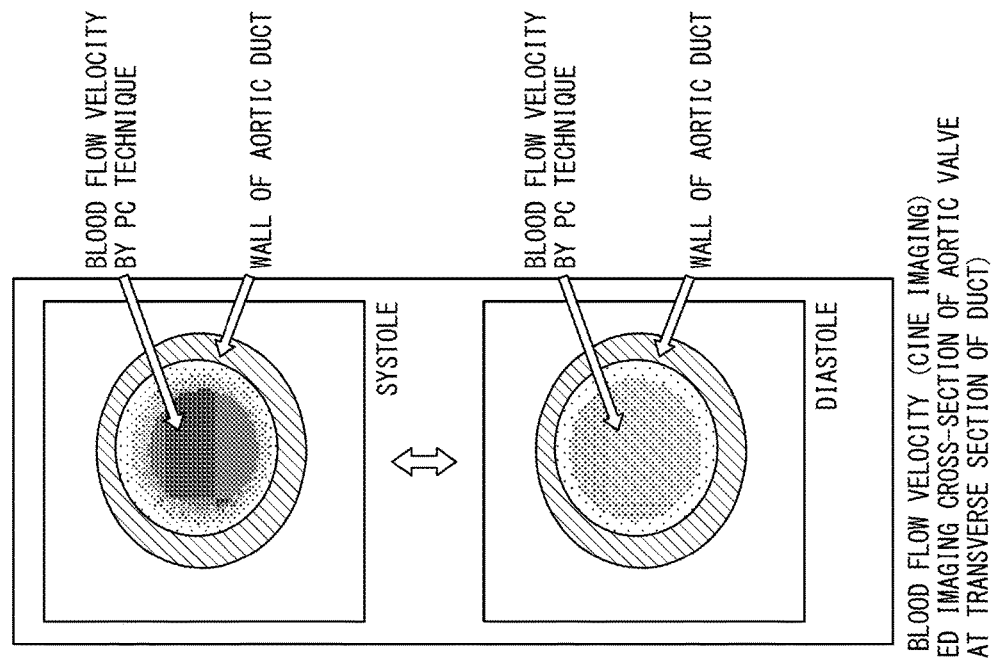
FIG. 13B is a chart showing an example of images of blood flow velocity obtained by performing cine imaging on the determined imaging cross-section of the aortic duct with the use of a PC technique.
Figure 13A:
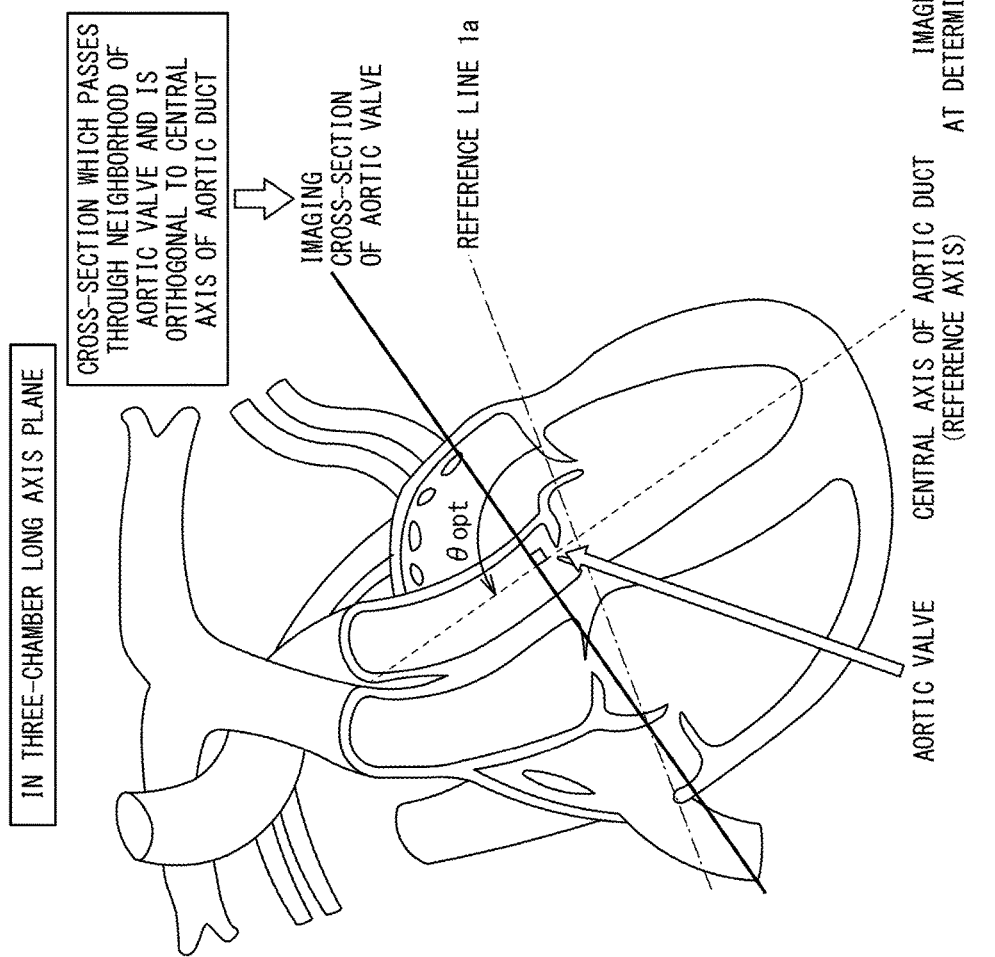
FIG. 13A is a chart showing an example of a method of determining the imaging cross-section of the aortic duct.

FIG. 13B is a chart showing an example of performing cine imaging on the transverse section of the aortic duct with the use of the PC technique and imaging blood flow velocity from the obtained image data. FIG. 13B schematically shows that the deep color region inside the aortic duct wall corresponds to a region of a fast blood flow velocity and the light-colored region corresponds to a region of a slow blood flow velocity.

The imaging cross-sections determined in the step ST26 such as the imaging cross-section of the aortic duct are cross-sections orthogonal to the central axis of the aortic duct. Therefore, the velocity of blood flowing inside the aortic duct can be accurately measured, as compared with a case where the imaging cross-section is determined obliquely to the central axis of the aortic duct.

Moreover, analysis of blood flow amount is performed in the step ST30 on an as-needed basis. This analysis is performed by the image analyzing unit 114 in FIG. 2. In the step ST28, the blood flow velocity inside the aortic duct can be measured. Meanwhile, square measure of the transverse section of the flow passage of the aortic duct can be calculated on the basis of the captured image. Then, blood flow amount (amount of blood passing per unit time) passing the imaging cross-section of the aortic duct can be calculated by using the blood flow velocity inside the aortic duct and the square measure of the transverse section of the flow passage of the aortic duct. In setting of a region of interest (or a cross-section) used for calculating the blood flow velocity and the blood flow amount, the previously detected position of the aortic valve can be used.

Moreover, for example, the blood flow amount of the flow passage of the upstream side of the aortic valve (left ventricular outflow tract) and the blood flow amount of the flow passage of the downstream side of the aortic valve (aortic duct) can be respectively calculated on the basis of the two imaging cross-sections sandwiching the aortic valve. Accordingly, symptomatic state such as regurgitation in the aortic valve can be diagnosed on the basis of behavior of these blood flow amounts.

Incidentally, the imaging cross-section of the aortic duct and the reference axis (central axis of the aortic duct) do not necessarily need to be strictly orthogonal to each other, but they may be substantially orthogonal to each other. In other words, they may deviate from a perfect orthogonal state within an allowable range of measuring blood flow velocity and analyzing blood flow amount accurately.

As mentioned above, according to the magnetic resonance apparatus 1 of the first embodiment, the amount of information to be inputted by an operator can be drastically reduced and complicated operation processes such as the chain oblique technique can be eliminated. For example, imaging cross-sections useful for diagnosis of the aortic valve and kinetic observation of blood inside the aortic duct can be determined in a short time, by inputting only information that the observation region is the aorta and the aortic duct.

In addition, positions of imaging cross-sections can be determined with high accuracy, because accumulation of errors like the conventional chain oblique technique in which a process of imaging and a process of setting a cross-section are repeated does not occur.

(3) Modified Version of The First Embodiment

In the aforementioned first embodiment, the magnetic resonance imaging apparatus 1 automatically determines the imaging cross-section of the aortic valve and the imaging cross-section of the aortic duct in the front and back of the aortic valve. The same method can be applied to valves inside the heart other than the aortic valve and bloodstream ducts connecting to this valve.

Figure 14:
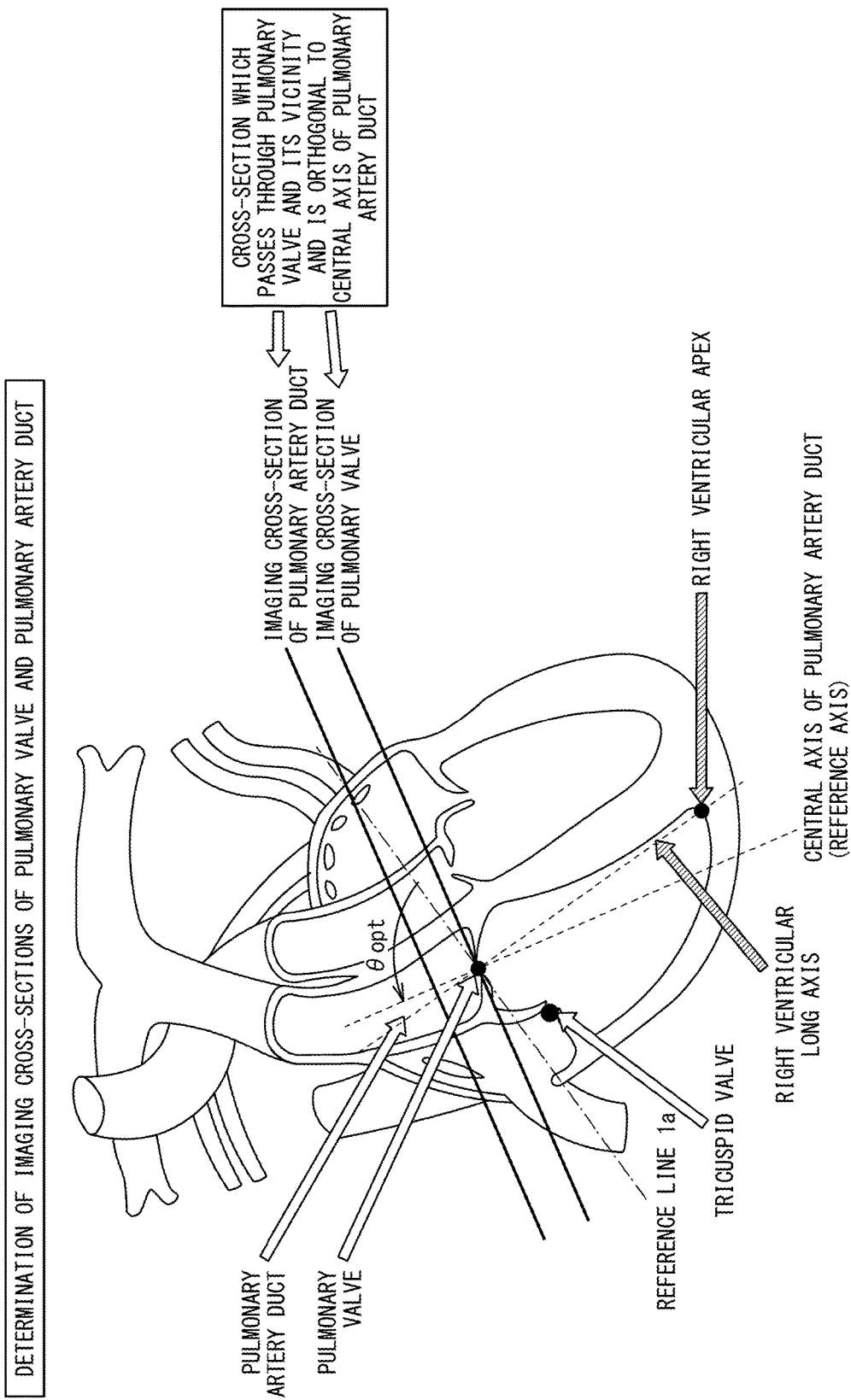
FIG. 14 is a diagram explaining a method of determining the imaging cross-section of the pulmonary valve.

For example, as shown in FIG. 14, the transverse section of the pulmonary valve can be determined as the imaging cross-section, in the same method as above. Alternatively, the imaging cross-section of the pulmonary artery duct connecting to the front and back of the pulmonary artery or the right ventricular outflow tract can be similarly determined. In this case, the characteristic region detecting unit 104 determines the respective positions of the pulmonary valve, the tricuspid valve and the right ventricular apex by using the aforementioned method based on the machine learning technique or the like in the step ST16 of FIG. 4. Then, the reference plane/reference axis determining unit 106 determines a cross-section passing through the respective centers of the pulmonary valve, the tricuspid valve and the right ventricular apex, as a reference plane instead of the three-chamber long axis plane in the step ST18. After this, the reference axis (central axis of the pulmonary artery duct), which passes through the center of the pulmonary valve and is in parallel with the wall of the pulmonary artery duct, is determined within this reference plane. When determining the central axis of the pulmonary artery duct, a right ventricular long axis passing through both of the right ventricular apex and the pulmonary valve, and a reference line 1a orthogonal to the right ventricular long axis in the reference plane are used as shown in FIG. 14.

Then, the cross-section, which is orthogonal to the central axis of this pulmonary artery duct and passes through the center of the pulmonary valve, is determined as the imaging cross-section of the pulmonary valve in the way similar to the step ST22. In addition, the cross-section, which is orthogonal to the central axis of this pulmonary artery duct and passes through the front and back of the pulmonary valve, is determined as the imaging cross-section of the pulmonary duct in the way similar to the step ST26.

Figure 15:
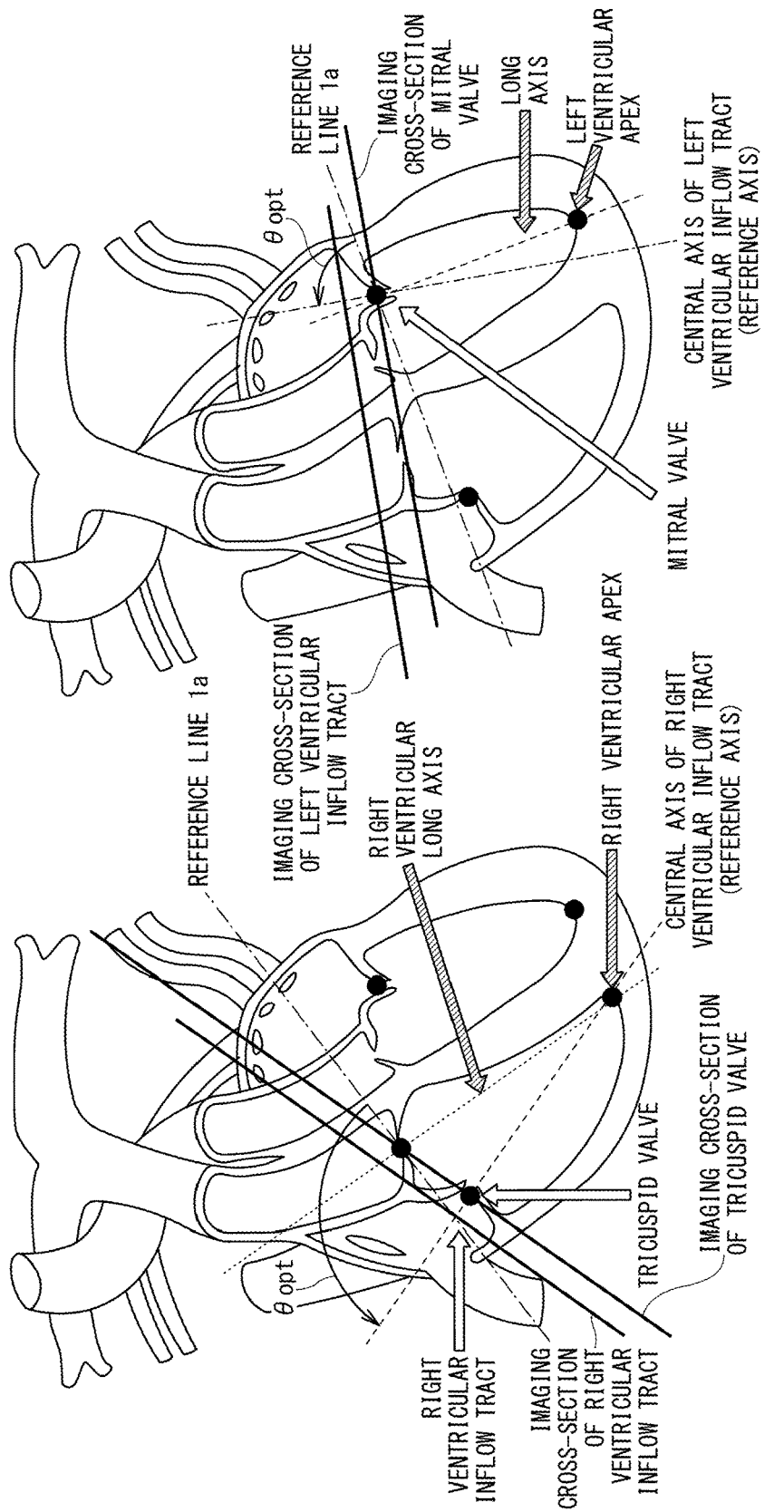
FIG. 15A is a diagram explaining a method of determining the respective imaging cross-sections of the tricuspid valve and the right ventricular inflow tract.
FIG. 15B is a diagram explaining a method of determining the respective imaging cross-sections of the mitral valve and the left ventricular inflow tract.

In addition, as shown in FIG. 15A, the transverse section of the tricuspid valve can be determined as the imaging cross-section, in the way similar to the first embodiment. In addition or alternatively, the transverse section of the bloodstream duct (right ventricular inflow tract) in the upstream side of the tricuspid valve and the transverse section of the bloodstream duct in the downstream side of the tricuspid valve can be similarly determined as the imaging cross-sections. In this case, the reference plane is the cross-section passing through the respective centers of the pulmonary valve, the tricuspid valve and the right ventricular apex, and the reference axis (central axis of the right ventricular inflow tract) is the axis in parallel with the wall of the right ventricular inflow tract.

Furthermore, as shown in FIG. 15B, a transverse section of the mitral valve can be determined as the imaging cross-section, in the same method as the first embodiment. In addition or alternatively, the transverse section of the bloodstream duct (left ventricular inflow tract) in the upstream side of the mitral valve and the transverse section of the bloodstream duct in the downstream side of the mitral valve can be similarly determined as the imaging cross-section. In this case, the reference plane is the cross-section (three-chamber long axis plane) passing through the respective centers of the mitral valve, the pulmonary valve and the left ventricular apex, and the reference axis (central axis of the left ventricular inflow tract) is the axis in parallel with the wall of the left ventricular inflow tract.

According to the first embodiment and its modified embodiments, the imaging cross-sections of the four valves (the mitral valve, the aortic valve, the pulmonary valve and the tricuspid valve) inside the heart can be automatically determined with high positional accuracy in a short time, without relying on skills of an operator. Accordingly, the first embodiment and its modified embodiments enable prompt and appropriate diagnosis of each cardiac valve in terms of shape and function.

In addition, velocity information on blood flowing inside a bloodstream duct and its flow amount can be accurately obtained from image information of the imaging cross-section perpendicular to the bloodstream path in the front or back of each valve. As a result, because the flow volume of blood outflowing from the heart to the lungs and the body of a patient and the flow volume of blood inflowing from the lungs and the body to the heart can be analyzed in a short time, the dynamic behavior of bloodstream of the entire heart can be precisely diagnosed.

Incidentally, the positions of the aortic valve and so on (hereinafter, the four valves inside the heart are collectively referred to as the aortic valve, etc.) changes depending on time phases of systole and diastole in a precise sense. Then, in the first embodiment and its modified embodiments, for example, three-dimensional data are acquired by performing multi-slice imaging at the time phase with comparatively little movement such as diastole. After this, images of the aortic valve, etc. can be obtained by imaging the aortic valve at the imaging cross-section in the vicinity of the aortic valve, etc. in addition to imaging the imaging cross-sections of each central position of the aortic valve, etc. determined based on these three-dimensional data, even if its position changes depending on time phase.

(4) The Second Embodiment

In contrast, in the second embodiment, each central position of the aortic valve, etc. changing depending on time phase is preliminarily calculated per time phase, and each position of the imaging cross-section passing through each center of the aortic valve, etc. is preliminarily determined so as to be associated with time phase. Then, when cine imaging is performed on the aortic valve, etc., imaging is performed at the position of the imaging cross-section associated with the time phase, which is determined by electrocardiographic synchronization signals such as R-wave or the like. According to this method, imaging at each time phase can be performed at the cross-section passing through the center of the aortic valve, etc., even if the position of the aortic valve, etc. changes depending on time phase.

Incidentally, the structure of the magnetic resonance apparatus of the second embodiment is basically the same as that of the first embodiment (see FIG. 1 and FIG. 2).

Figure 16:
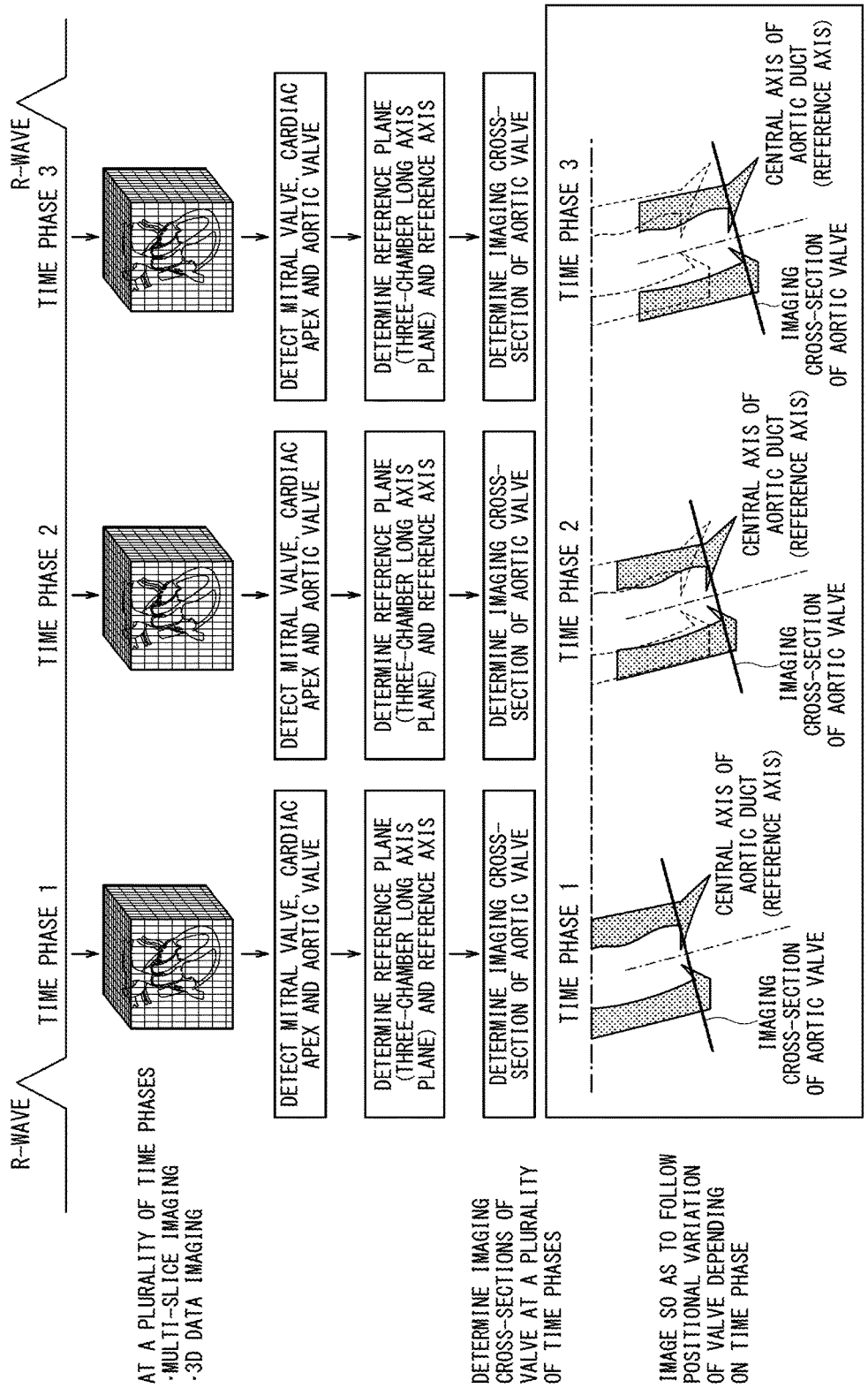
FIG. 16 is a diagram explaining a method of determining imaging cross-sections in the second embodiment.

FIG. 16 is a diagram showing the general outline of operation of the second embodiment. In the second embodiment, multi-slice imaging is performed on the heart at a plurality of time phases, and thereby three-dimensional data per time phase are generated by the 3D data generation unit 102. Then, the characteristic region detecting unit 104 detects positions of a plurality of characteristic regions of the mitral valve, the left ventricular apex and the aortic valve, etc. per time phase from these three-dimensional data per time phase. After this, the reference plane/reference axis determining unit 106 determines the reference plane and the reference axis per time phase. In addition, the imaging cross-section determining unit 108 determines the imaging cross-section of the aortic valve, etc. per time phase, on the basis of the reference plane and the reference axis determined per time phase. The methods of determining the reference plane and the reference axis and the methods of determining imaging cross-sections of the aortic valve, etc. are similar to the method of the first embodiment.

Then, cine imaging on the aortic valve, etc. is performed at each imaging cross-section determined per time phase. According to the second embodiment, because the position of each imaging cross-section of the aortic valve, etc. tracks the central position of each of the aortic valve, etc. which change depending on time phase (i.e. the position of each imaging cross-section varies in accordance with the moving central position), images that precisely depict the central position of the aortic valve, etc. can be obtained.

Incidentally, when the direction of each of the imaging cross-sections (or the direction of the normal vector of each of the imaging cross-sections) is firstly set so as to be aligned in a direction of the imaging cross-section of any one of time phases in determination of the imaging cross-section at each time phase, then only the offset position of the imaging cross-section (the position along the central axis direction of the aortic duct) may be adjusted to track the central position of each of the aortic valve, depending on the time phases.

(5) The Third Embodiment

Figure 17:
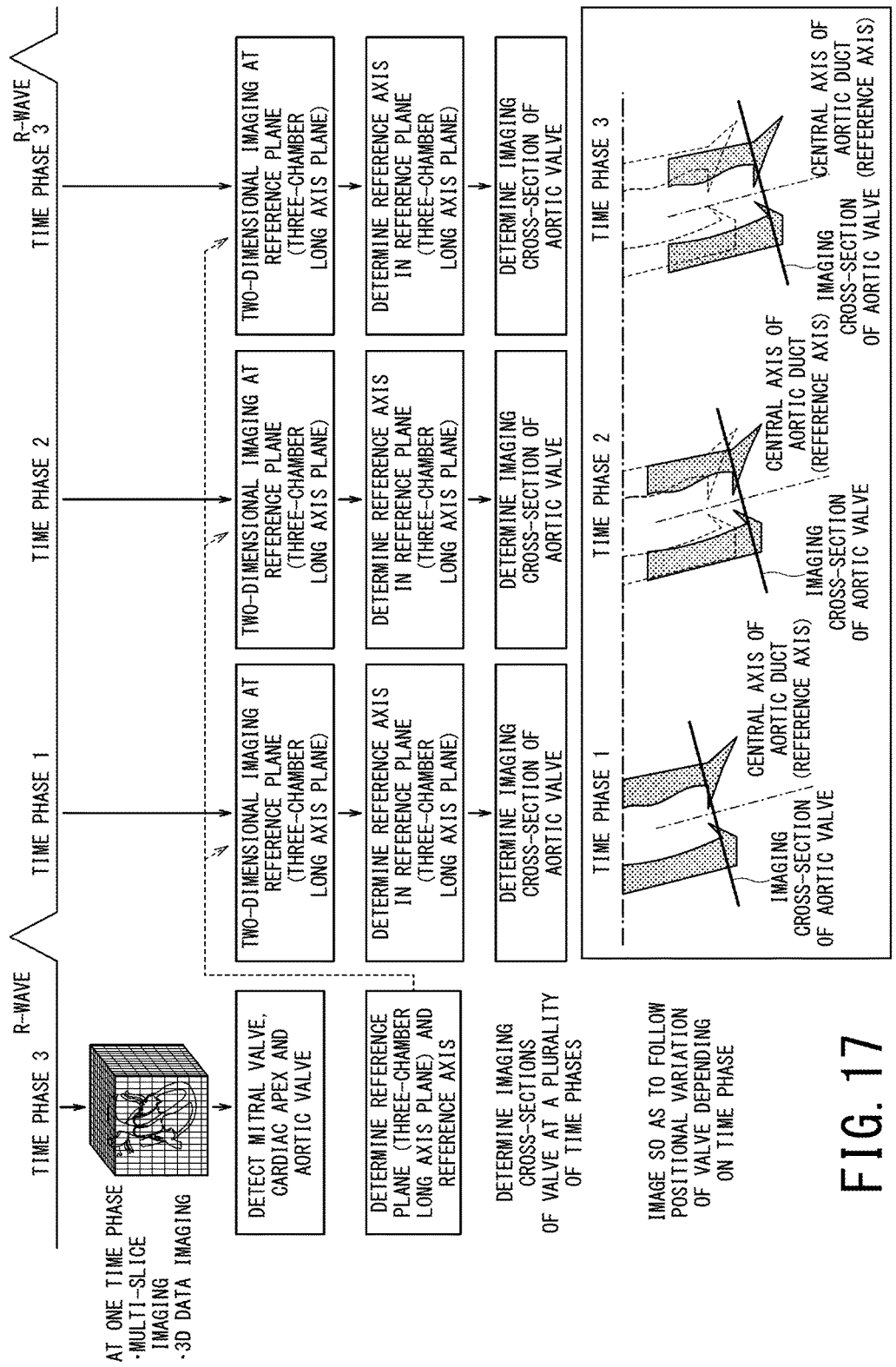
FIG. 17 is a diagram explaining a method of determining imaging cross-sections in the third embodiment.

FIG. 17 is a diagram showing the general outline of operation of the third embodiment. The structure of the magnetic resonance apparatus of the third embodiment is the same as that of the first embodiment and the second embodiment.

In the third embodiment, multi-slice imaging is performed on the heart at one time phase, for example, at a time phase of diastole with little movement, and the 3D data generation unit 102 generates one set of three-dimensional data corresponding to this one time phase. Then, the characteristic region detecting unit 104 detects positions of characteristic regions from the one set of three-dimensional data, and the reference plane/reference axis determining unit 106 determines one reference plane on the basis of the detected characteristic regions. For example, in the case of imaging the aortic valve, positions of the three characteristic regions (i.e., the aortic valve, the mitral valve and the left ventricular apex) are detected and a cross-section (three-chamber long axis plane) passing through these three characteristic regions is determined as a reference plane. The processing up to this determination is basically the same as the first embodiment and corresponds to the step ST10 to step ST18 in FIG. 4. However, in the third embodiment, the subsequent processing is different from the first embodiment.

In the third embodiment, two-dimensional imaging is performed on the determined reference plane (three-chamber long axis plane) at a plurality of time phases. Then, the characteristic region detecting unit 104 detects the central position of the aortic valve per time phase from the two-dimensional images obtained per time phase. In addition, the reference plane/reference axis determining unit 106 determines the central axis of the aortic duct per time phase. Moreover, the imaging cross-section determining unit 108 determines the imaging cross-sections which respectively correspond to the respective time phases during imaging. After this, cine imaging is performed on the aortic valve, etc. at the imaging cross-sections determined per time phase.

In the third embodiment, similarly to the second embodiment, imaging can be performed so as to follow the central position of the aortic valve, etc., even if the central positions vary depending on time phase, resulting that images in which each central position of the aortic valve, etc. is precisely depicted can be obtained. In addition, because images for determining imaging positions per time phase in the third embodiment are obtained not from the three-dimensional images like the second embodiment but from the two-dimensional images, imaging time and image processing time for determining imaging positions per time phase can be shortened in the third embodiment.

Incidentally, similarly to the second embodiment, when the direction of each of the imaging cross-sections (or the direction of the normal vector of each of the imaging cross-sections) is firstly set so as to be aligned in a direction of the imaging cross-section of any one of time phases in determination of the imaging cross-section at each time phase, then only the offset position of the imaging cross-section (the position along the central axis direction of the aortic duct) may be adjusted to track the central position of each of the aortic valve, depending on the time phases.

As described above, according to the magnetic resonance apparatus 1 of each embodiment, in addition to the well-known six reference planes, cross-sections useful for cardiac diagnosis such as a cross-section appropriate for kinetic observation of the aortic valve, a transverse section of a bloodstream duct appropriate for understanding cardiac hemodynamics and so on can be determined automatically and accurately in a short time without relying on experience and skills of an operator.

So far, technology of automatically setting transverse sections of bloodstream ducts such as an aorta and pulmonary artery, transverse sections at positions of the aortic valve and the pulmonary valve has been explained. However, the applicability of the technology of each of the aforementioned embodiments is not limited to the above. For example, the technology of the aforementioned embodiments can be applied to a tubular structure like the intestines. For example, the magnetic resonance apparatus 1 of the above embodiments can be constituted so as to (a) detect specified characteristic regions inside the tubular structure, (b) calculate the central axis of the tubular structure base on evaluation with the use of the positions of the characteristic regions and the gradient of pixel values of three-dimensional data of the tubular structure, (c) identify the cross-sectional position of the cross-section orthogonal to this central axis, and (d) image the cross-section at the specified cross-sectional position.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   a gantry which includes a static field magnet, a gradient coil and an RF coil to image an object;
   processing circuitry; and
   a memory that stores processor-executable instructions which, when executed by the processing circuitry, cause the processing circuitry to
   detect at least one position of an aortic valve and a pulmonary valve from three-dimensional image data including a heart of the object, as at least one characteristic region inside the heart,
   specify a position of an imaging cross-section substantially orthogonal to a bloodstream path inside the heart based on the position of the aortic valve or the pulmonary valve, and
   cause the gantry to image the imaging cross-section of the object at the specified position of the imaging cross-section;
   wherein the imaging cross-section substantially orthogonal to the bloodstream path inside the heart is a transverse section of a predetermined valve, a transverse section in a vicinity of the predetermined valve or a transverse section of a bloodstream duct connected to the predetermined valve.

2. The apparatus according to claim 1, wherein the processing circuitry is caused to
   detect positions of at least three anatomical characteristic regions, and
   determine a cross-section including the positions of the three anatomical characteristic regions as a reference plane, and to specify a position of a cross-section substantially orthogonal to a reference axis included in the reference plane as the position of the imaging cross-section.

3. The apparatus according to claim 2, wherein the processing circuitry is caused to
determine a central axis of the bloodstream duct passing through a position of the predetermined valve, and
set a central axis of the bloodstream duct as the reference axis.

4. The apparatus according to claim 3, wherein the processing circuitry is caused to
calculate a gradient of pixel values of a region including a wall of the bloodstream duct based on image data of the reference plane, and
determine an inclination of the central axis of the bloodstream duct so that a direction of the central axis of the bloodstream duct becomes substantially orthogonal to a direction of the gradient of pixel values.

5. The apparatus according to claim 2, wherein:
the reference plane is a three-chamber long axis plane passing through a mitral valve, a left ventricular apex and an aortic valve;
the predetermined valve is the aortic valve; and
the bloodstream duct is an aortic duct connected to the aortic valve.

6. The apparatus according to claim 2, wherein:
the reference plane is a cross-section passing through a pulmonary valve, a tricuspid valve and a right ventricular apex,
the predetermined valve is the pulmonary valve, and
the bloodstream duct is a pulmonary artery duct connected to the pulmonary valve.

7. The apparatus according to claim 2, wherein:
the reference plane is a three-chamber long axis plane passing through a mitral valve, a left ventricular apex and an aortic valve,
the predetermined valve is the mitral valve, and the bloodstream duct is connected to the mitral valve.

8. The apparatus according to claim 2, wherein:
the reference plane is a cross-section passing through a pulmonary valve, a tricuspid valve and a right ventricular apex,
the predetermined valve is the tricuspid valve, and
the bloodstream duct is connected to the tricuspid valve.

9. The apparatus according to claim 2, wherein the processing circuitry is caused to detect the positions of the at least three anatomically characteristic regions by using a method based on machine learning.

10. The apparatus according to claim 9, wherein the processing circuitry is caused to detect the positions of the at least three anatomically characteristic regions by using a method based on template matching.

11. The apparatus according to claim 1,
wherein the processing circuitry is caused to cause the gantry to perform cine imaging on the imaging cross-section including the transverse section of the predetermined valve or the transverse section in the vicinity of the predetermined valve.

12. The apparatus according to claim 11, wherein the processing circuitry is caused to cause the gantry to perform the cine imaging based on an imaging technique of FE (Field Echo) type or SSFP 5 (Steady State Free Precession).

13. The apparatus according to claim 1, wherein the processing circuitry is caused to cause the gantry to perform imaging on the imaging cross-section including the transverse section of a bloodstream duct connected to the predetermined valve, by using an imaging technique capable of acquiring information on blood flow velocity.

14. The apparatus according to claim 13, wherein the imaging technique capable of acquiring information on blood flow velocity is a phase contrast technique.

15. The apparatus according to claim 13, wherein the processing circuitry is caused to analyze cardiac hemodynamics including analysis of blood flow amount, based on the information on blood flow velocity and information on a diameter size of the bloodstream duct.

16. The apparatus according to claim 1, wherein:
the three-dimensional data include plural sets of three-dimensional data generated from magnetic resonance signals respectively acquired at different cardiac time phases so that each of the plural sets corresponds to each of the different cardiac time phases; and
the processing circuitry is caused to
detect positions of a plurality of anatomically characteristic regions inside the heart from the plural sets of three-dimensional data per cardiac time phase,
specify imaging cross-sections per cardiac time phase; and
cause the gantry to image the imaging cross-sections specified per cardiac time phase.

17. A magnetic resonance imaging method comprising:
detecting at least one position of an aortic valve and a pulmonary valve from three-dimensional image data including a heart of the object, as at least one characteristic region inside the heart,
specifying a position of an imaging cross-section substantially orthogonal to a bloodstream path inside the heart based on the position of the aortic valve or the pulmonary valve, and
imaging the imaging cross-section of the object at the specified position of the imaging cross-section,
wherein the imaging cross-section substantially orthogonal to the bloodstream path inside the heart is a transverse section of a predetermined valve, a transverse section in a vicinity of the predetermined valve or a transverse section of a bloodstream duct connected to the predetermined valve.

18. A magnetic resonance imaging apparatus comprising:
a gantry which includes a static field magnet, a gradient coil and an RF coil to image an object;
processing circuitry; and
a memory that stores processor-executable instructions that, when executed by the processing circuitry, cause the processing circuitry to
detect at least one characteristic region from three dimensional data including a tubular structure of an object,
calculate a central axis of the tubular structure based on an evaluation function including a gradient direction of pixel values of the three-dimensional data, and to specify a position of an imaging cross-section orthogonal to the central axis, and
cause the gantry to image the imaging cross-section of the object at the specified position of the imaging cross-section.

19. The magnetic resonance imaging apparatus according to claim 18, wherein the processing circuitry is caused to calculate the central axis by using an evaluation function taking a maximum value when a gradient direction of a duct wall of the tubular structure is orthogonal to the central axis.

* * * * *